(12) United States Patent
Mumper et al.

(10) Patent No.: US 7,153,525 B1
(45) Date of Patent: Dec. 26, 2006

(54) MICROEMULSIONS AS PRECURSORS TO SOLID NANOPARTICLES

(75) Inventors: Russell John Mumper, Lexington, KY (US); Michael Jay, Lexington, KY (US)

(73) Assignee: The University of Kentucky Research Foundation, Lexington, KY (US)

( * ) Notice: Subject to any disclaimer, the term of this patent is extended or adjusted under 35 U.S.C. 154(b) by 334 days.

(21) Appl. No.: 09/812,884

(22) Filed: Mar. 21, 2001

Related U.S. Application Data

(60) Provisional application No. 60/191,112, filed on Mar. 22, 2000.

(51) Int. Cl.
*A61K 9/14* (2006.01)
*B29B 9/00* (2006.01)

(52) U.S. Cl. ............... 424/489; 424/450; 424/499; 514/937; 514/939; 264/5

(58) Field of Classification Search ........ 424/489–491, 424/499, 450, 401, 498, 400; 514/937–939, 514/393; 264/4.1–4.4, 5
See application file for complete search history.

(56) References Cited

U.S. PATENT DOCUMENTS

| | | | |
|---|---|---|---|
| 4,273,672 A | 6/1981 | Vassiliades | 452/316 |
| 4,652,441 A | 3/1987 | Okada et al. | 424/19 |
| 4,826,689 A | 5/1989 | Violanto et al. | 424/489 |
| 4,997,599 A | 3/1991 | Steiner et al. | 264/5 |
| 5,049,322 A | 9/1991 | Devissguet et al. | 264/4.1 |
| 5,051,304 A | 9/1991 | David et al. | 428/402.2 |
| 5,133,908 A | 7/1992 | Stainmesse et al. | 264/4.1 |
| 5,145,684 A * | 9/1992 | Liversidge et al. | 424/490 |
| 5,213,788 A * | 5/1993 | Ranney | 424/9 |
| 5,250,236 A | 10/1993 | Gasco | 264/4.4 |
| 5,500,224 A | 3/1996 | Vranckx et al. | 424/451 |
| 5,510,118 A * | 4/1996 | Bosch et al. | 424/489 |
| 5,542,935 A | 8/1996 | Unger et al. | 604/190 |
| 5,658,575 A * | 8/1997 | Ribier et al. | 424/401 |
| 5,672,358 A | 9/1997 | Tabibi et al. | 424/459 |
| 5,733,526 A | 3/1998 | Trevino et al. | 424/9.52 |
| 5,744,155 A | 4/1998 | Friedman et al. | 424/434 |
| 5,766,635 A | 6/1998 | Spenleuhauer et al. | 424/489 |
| 5,879,715 A | 3/1999 | Higgins et al. | 424/489 |
| 6,139,870 A | 10/2000 | Verrecchia | 424/450 |
| 6,203,802 B1 | 3/2001 | Handjani et al. | 424/401 |
| 6,238,694 B1 | 5/2001 | Gasco | 424/450 |
| 6,245,349 B1 * | 6/2001 | Yiv et al. | 424/450 |
| 6,551,619 B1 * | 4/2003 | Penkler et al. | 424/489 |

FOREIGN PATENT DOCUMENTS

| | | |
|---|---|---|
| EP | 0 506 197 A1 * | 9/1992 |
| WO | WO 99/27918 | 6/1999 |
| WO | WO 00/06120 | 2/2000 |
| WO | WO 00/30620 | 6/2000 |
| WO | WO 00/74658 | 12/2000 |
| WO | WO 01/78689 | 10/2001 |

OTHER PUBLICATIONS

Agostiano, A. et al ("Synthesis and structural characterisation of CdS nanoparticles prepared in a four-components "water-in-oil" micromeulsion", Micron, 31:253-258,2000.*
Gasco, M. R. Solid Lipid Nanospheres from Warm Micro-Emulsion, Dec. 1997, vo. 9, No. 11, pp. 52-58.*
Agostiano, A. et al., "Synthesis and structural characterisation of CdS nanoparticles prepared in a four-components "water-in-oil" microemulsion", Micron, 31:253-258, 2000.
Ando S. et al., "PLGA microspheres containing plasmid DNA: preservation of supercoiled DNA via cryopreparation and carbohydrate stabilization", J. Pharm. Sci., 88:126-30, 1999.
Bhargave, H.N. et al., "Using microemulsions for drug delivery", Pharm. Tech., Mar. 1987, pp. 46-53.
Bocca, C. et al, "Phagocytic uptake of fluorescent stealth and non-stealth solid lipid nanoparticles", International Journal of Pharmaceutics, 175, 185-193, 1998.
Capek, I., "Microemulsion polymerization of styrene in the presence of anionic emulsifier", Advances in Colloid and Interface Science, 82:253-273, 1999.
Cavalli R. et al., "Solid lipid nanoparticles as carrier of hydrocortisone and progesterone complexes with cyclodextrins," International Journal of Pharmaceutics, 182:59-69, 1999.
Contantinides, P.P., Lipid microemulsions for improving drug dissolution and oral absorption: physical and biopharmaceutical aspects, Pharm. Res. 12:1561-1572, 1995.
Cornelius, C. et al., "Improved control over particle sizes and stability of concentrated fluorocarbon emulsions by using mixed fluorocarbon/hydrocarbon molecular dowels", Artif, Cells Blood Sub. Immobil. Biotech, 22:1183-1191, 1994.
Corr, M. et al., "Gene vaccination with naked plasmid DNA: mechanism of CTL priming", J. Exp. Med., 184 (1996) 1555-1560.
Corr M. et al., "In vivo priming by DNA injection occurs predominantly by antigen transfer", J. Immunol., 163 (1999) 4721-4727.
Degano, P. et al., "Intradermal DNA immunization of mice against influenza A virus using the novel Powderject system", Vaccine, 16 (1998) 394-398.
Doe, B. et al., "Induction of cytotoxic T lymphocytes by intramuscular with plasmid DNA is facilitated by bone marrow-derived cells", Proc. Natl. Acad. Sci. USA, 93 (1996) 8578-8583.

(Continued)

*Primary Examiner*—Michael Hartley
*Assistant Examiner*—Micah-Paul Young
(74) *Attorney, Agent, or Firm*—Fulbright & Jaworski L.L.P.

(57) ABSTRACT

The preparation of novel microemulsions to be used as precursors for solid nanoparticles is described. The microemulsion precursors consist of either alcohol-in-fluorocarbon microemulsions, liquid hydrocarbon-in-fluorocarbon microemulsions, or liquid hydrocarbon-in-water microemulsions. The formed solid nanoparticles have diameters below 200 nanometers and can be made to entrap various materials including drugs, magnets, and sensors. The solid nanoparticles can be made to target different cells in the body by the inclusion of a cell-specific targeting ligand. Methods of preparing the novel microemulsion precursors and methods to cure solid nanoparticles are provided.

10 Claims, 23 Drawing Sheets

OTHER PUBLICATIONS

Fan, H. et al., "Immunization via hair follicles by topical application of naked DNA to normal skin", Nat Biotechnol., 17 (9) (1999) 870-872.

Fang, J. et al., "Nanocrystalline bismuth synthesized via an in situ polymeration-microemulsion process" Materials Letters, 42:113-120, 2000.

Fynan, E.F. et al., "DNA vaccines: protective immunizations by parental, mucosal and gene-gun inoculations", Proc. Natl. Acad. Sci., USA, 90 (1993) 11478-11482.

Gauger, P.G. et al., "Initial experience with partial liquid ventilation in pediatric patients with the acute respiratory distress syndrome", Crit. Care Med., 24:16-22, 1996.

Gerdts, V. et al., "Protection of pigs against Aujesky's disease by DNA vaccination", J. Gen Virol., 78 (Pt 9) (1997) 2139-46.

Hara, T. et al., "Emulsion formulations as a vector for gene delivery in vitro and in viro", Advanced Drug Delivery Reviews 24 (1997), 265-271.

Ho H.O. et al., "Preparation of microemulsions using polyglycerol fatty acid esters as surfactant for the delivery of protein drugs", J. Pharm. Sci., 85:138-143, 1996.

Huang, A.Y.C. et al., "Role of bone marrow derived cells in presenting MHC class I-restricted tumor antigens", Science, 264 (1994) 961-965.

Jono, K. et al., "Preparation of lecithin microcapsules by a dilution method using the Wurster process for intraarterial administration in gadolinium neutron capture therapy", Chem. Pharm. Bull., 47(1):54-63, 1999.

Kwoh, D.Y. et al., "Stablization of poly-L-lysine/DNA polyplexes for in vivo gene delivery to the liver", Biochim. Biophys. Acta., 1444:171-190, 1999.

Lade, M. et al., "On the nanoparticle synthesis in microemulsions: detailed characterization of an applied reaction mixture", Colloids and Surfaces A: Physicochemical and Engineering Aspects, 163:3-15, 2000.

Lattes, A. et al., "Microemulsions of perfluorinated and semifluorinated compounds" Art. Cells. Blood Subs. Immob. Biotech., 22:1007-1018, 1994.

Li, Y. et al., "Particle size distribution in the synthesis of nanoparticles using microemulsions", Langmuir, 15:952-956, 1999.

Liu, M.A., "The immunologist's grail: Vaccines that generate cellular immunity", Proc. Natl. Acad. Sci. USA, 94:10496-10498, 1997.

MacLaughlin, F.C. et al., "Chitosan and depolymerized chitosan oligomers as condensing carriers for in-vivo plasmid delivery", J. Controlled Rel., 56:259-272, 1998.

Meier W., "Nanostructure synthesis using surfactants and copolymers", Current Opinion in Colloid & Interface Science, 4:6-14, 1999.

Meijer, D.K.F. et al., "Targeting of drugs to the liver", Sem. Liv. Dis., 15:202-256, 1995.

Miyamoto, M. et al., "Biodistribution of gadolinium incorporated in lipid emulsions intraperitoneally adminstered for neutron-capture therapy with tumor-bearing hamsters", Biol. Pharm. Bull., 22(12):1331-134, 1999.

Mumper, R.J. et al. , "Controlled Plasmid Delivery and Gene Expression: Applications for Nucleic Acid-Based Vaccines", DNA Vaccines: Methods and Protocols, DB Lowrie and R Whalen ( Eds.), Humana Press, Inc., Totowa, NJ, 1999, Chapter 24, pp. 267-286.

Mumper, R.J. et al., "Polymeric Gene Delivery Systems for In-Vivo Gene Therapy", Advanced Gene Delivery: From Concepts to Pharmaceutical Products, AP Rolland (Ed.), Harwood Academic Publishers, Amsterdam, The Netherlands, (1999), pp. 143-173.

Munshi, N. et al., "Preparation and size modulation of drug loaded nanoencapsulated particles using microemulsion mediated method", Journal of Controlled Release, 41:57, 1997.

Pertmer, T.M. et al., "Gene gun-based nucleic acid immunization: elicitation of humoral and cytotoxic T lymphocytes responses following epidermal delivery of nanogram quantities of DNA", Vaccine, 13 (1995) 1427-1430.

Porta, F., et al., "Synthesis of spherical nanoparticles of Cu2L2O5 (L=Ho, Er) from W/O microemulsions", Colloids and Surfaces A: Physiochemical and Engineering Aspects, 160:281-290, 1999.

Riess, J.G. et al., "Advanced fluorocarbon-based systems for oxygen and drug delivery, and diagnosis", Art. Cells. Blood Subs. Immob. Biotech., 25:43-52, 1997.

Robinson, H.L. et al., "C.A.T. DNA vaccines", Sen. Immunology, 9:271-283, 1997.

Ruys, A.J. et al., "The nanoparticle-coating process: a potential sol-gek route to homogeneous nanocomposites", Materials Sciences and Engineering, 265:202-207, 1999.

Shi, Z. et al., "DNA-based non-invasive vaccination onto the skin", Vaccine, 17 (17) (1999) 2136-41.

Singh, M. et al., "Cationic microparticles: A potent delivery system for DNA vaccines", Proc. Natl. Acad. Sci. USA, 97 (2) (2000) 811-6.

Sliedregt, L.A. et al., "Design and synthesis of novel amphiphilic dendritic galactosides for selective targeting of liposomes to the hepatic asialoglycoprotein receptor", J. Med. Chem., 25:609-618, 1999.

Song, K.C. et al., "Preparation of high surface area tin oxide powders by a homogeneous precipation method", Materials Letters, 42:283-289, 2000.

Tang, Z., "Electrochemical synthesis of polyaniline nanoparticles", Electrochemistry Communications, 2:32-35, 2000.

Tang, D.C. et al., "Vaccination onto bare skin", Nature, 388 (1997) 729-730.

Tojo, C. et al., "Influence of reactant excess and film flexibility on the mechanism of nanoparticle formation in microemulsions: A Monte Carlo simulation", Langmuir, 14:6835-6839, 1998.

Tokumitsu, H. et al., "Gadolinium neutron-capture therapy using novel gadopentetic acid-chitosan complex nanoparticles: in vivo growth suppression of experimental melanoma solid tumor", Cancer Lett., 2000 150(2): 177-182, 2000.

Tokumitsu, H. et al., "Chitosan-gadopentetic acid complex nanoparticles for gadolinium neutron-capture therapy of cancer: preparation by novel emulsion-droplet coalescence technique and characterization", Pharm. Res., 16 (12):1830-1835, 1999.

Torres, C.A.T. et al., "Differential dependence on target site tissue for gene gun and intramuscular DNA immunizations", J. Immunol., 158 (1997) 4529-4532.

Truong-Le, V.L. et al., "Controlled gene delivery by DNA-gelatin nanospheres", Hum. Gene Ther., 10:1709-1717, 1998.

Ulmer, J.B. et al., "DNA vaccines", Cur. Opin. Immunol., 8(1996) 531-536.

Ulmer, J.B. et al., "Generation of MHC class I-restricted cytotoxic T lymphocytes by expression of a viral protein in muscle cells: antigen presentation by non-muscle cells", Immunology, 89 )1996) 59-67.

Van Drunen Little-van den hurk et al., "Intradermal immunization with a bovine herpesvius-1 DNA vaccine induces protective immunity in cattle", J. Gen. Viol., 79 (1998) 831-839.

Van Rooij, E.M., "Effect of vaccination route and composition of DNA vaccine on the incuction of protective immunity against pseudorabies infection in pigs", Vet Immunol Immunopathol, 66 (2) (1998) 113-26.

Wadhwa, M.S., et al., "Receptor mediated glycotargeting", J. Drug Target, 3:111-127, 1995.

Wang, D. et al., "Encapsulation of plasmid DNA in biodegradable poly(D, L-lactic-co-glycolic acid) microsphere as a novel approach for immunogene delivery", J. Cont. Rel., 57:9-18, 1999.

Xiangling, X. et al., "Growth of polymer nanoparticles in microemulsion polymerization initiated with ray", Radiation Physics and Chemistry, 54:279-283, 1999.

Yoshida, A. et al., "Advantage of gene gun-mediated over intramuscular inoculation of plasmid DNA vaccine in reproducible induction of specific immune respones", Vaccine, 18 (17) (2000) 1725-9.

Bargoni et al., "Solid lipid nanoparticles in lymph and plasma after duodenal administration to rats," *Pharmaceutical Research*, 15:745-750, 1998.

Cavalli et al., "Study by X-ray powder diffraction and differential scanning calorimetry of two model drugs, phenothiazine and nifedipine, incorporated into lipid nanoparticles," *Eur. J. Pharm. Biopharm.*, 41(5):329-333, 1995.

Cavalli et al., "The effect of the components of microemulsions on both size and crystalline structure of solid lipid nanoparticles (SLN) containing a series of model molecules," *Pharmazie*, 53(6):392-396, 1998.

De and Hoffman, "An ophthalmic formulation of a Beta-adrenoceptor antagonist, levobetaxolol, using Poly(acrylic acid) nanoparticles as carrier: loading and release studies," *Journal of Bioactive and Compatible Polymers*, 16:20-31, 2001.

Morel et al., "Thymopentin in solid lipid nanoparticles," *International J. of Pharmaceutics*, 132:259-261, 1996.

Sharma et al., "Novel taxol formulation: polyvinylpyrrolidone nanoparticle-encapsulated taxol for drug delivery in cancer therapy," *Oncology Research*, 8(7/8):281-286, 1996.

Ugazio et al., "Incorporation of cyclosporin A in solid lipid nanoparticles (SLN)," *International J. of Pharmaceutics*, 241:341-344, 2002.

Utreja et al., "Lipoprotein-mimicking biovectorized systems for methotrexate delivery," *Pharmaceutica Acta Helvetiae*, 73:275-279, 1999.

* cited by examiner

MICROEMULSIONS AS PRECURSORS TO SOLID NANOPARTICLES

CONTINUING DATA

The present application claims the benefit of priority to U.S. Provisional Application No. 60/191,112, filed Mar. 22, 2000, which is incorporated by reference herein in its entirety.

BACKGROUND OF THE INVENTION

1. Field of the Invention

The invention relates to making targeted nanoparticle delivery systems for drugs, magnets, and sensors. The invention relates to the preparation of microemulsion precursors whereby the dispersed droplets are templates for the curing of solid nanoparticles. The invention also relates to making solid nanoparticles from microemulsion precursors without the use of light, electricity, free-radicals, or γ-rays to make nanoparticles. The invention also relates to a nanoparticulate delivery system for delivering a molecule of interest to the body.

2. Brief Description of the Related Art

Nanotechnology is becoming increasingly more important in the pharmaceutical, chemical and engineering fields. This is primarily due to the fact that particles made at the nanoscale have much different physical, chemical, and biological properties than larger particles. For example, in the pharmaceutical field, nanoparticles have been used to more efficiently deliver drugs, genes, diagnostics, and vaccines (Douglas et al., 1987; MacLaughlin, et al., 1998; Kreuter 1995). Due to their small size, nanoparticles can aid in the direct entry of entrapped molecules into cells (either non-specifically or specifically via cell targeting ligands). Cellular uptake of drug molecules is often desirable and even necessary if the mechanism of action of the drug requires it to be in the cell as in the case of larger biologically-based molecules such as antisense oligonucleotides, ribozymes, and plasmid DNA. Further, the benefit of being able to deliver a vaccine antigen intracellularly to achieve a cellular-based immune response has been established (for a review see Mumper et al., 1999). However, getting these larger molecules efficiently into cells is difficult. Unlike small drugs, which may efficiently enter cells by diffusion and/or transport mechanisms, large molecules often require a carrier system to achieve sufficiently high intracellular concentrations. Nanoparticles may provide a way of increasing the cellular uptake of larger molecules if these molecules can be efficiently packaged into pharmaceutically acceptable carriers using a cost-effective method.

Gene therapy has emerged as a promising approach for the treatment of a number of genetic and acquired diseases. Non-viral gene therapy involves the delivery of genetic material (plasmid DNA) into cells of the body to produce therapeutic proteins endogenously by exploiting the cell's transcriptional and translational machinery. Most non-viral gene delivery strategies employ polyelectrolyte complexation using cationic lipids, peptides, or polymers to complex and condense negatively charged plasmid DNA into particles having diameters in the 100–1000 nm range. The complexation strategy is fraught with problems since: i) the cationic molecules are relatively toxic materials and are not approved by the FDA in any marketed medical product, ii) the complexes are prone to aggregation at or near charge neutrality, iii) stable particles having diameters below 100 nm are very difficult to engineer, iv) scale-up of these complexes is complicated and expensive since very controlled mixing systems are needed to introduce the ions in solution, and v) the complexes tend to aggregate or dissociate when injected in the body.

Although a few reports in the literature have demonstrated proof-of-concept in animals, attempts to specifically target polyelectrolyte complexes to cells in the body using cell-specific ligands have been largely unsuccessful. Also, no such technology has advanced to clinical testing in humans. Contributing factors to this lack of success may be that these ligands (i.e., monoclonal antibodies, carbohydrates, etc.) are attached to biologically unstable particles and/or that the these particles cannot be made small enough to be efficiently taken up by cells by receptor-mediated endocytosis.

As an alternative to polyelectrolyte complexation, researchers have also attempted to encapsulate plasmid DNA into conventional solid nanoparticles based on biodegradable polymers such as polylactic acid-co-glycolic acid (Ando et al., 1999; Wang et al., 1999), gelatin (Truong-Le, et al., 1998), and other polymers (Mumper and Klakamp, 1999). However, these techniques and systems have disadvantages such as: a) the relatively high cost of these carrier materials, b) the unknown safety of some of these materials, c) the use of rigorous processes typically used to make the nanoparticles (i.e., interfacial polymerization and/or high-torque mechanical mixing that may be damaging to biologically-based drugs and expensive to scale-up and manufacture), d) the inability to produce nanoparticles below 50 nm, and e) the low encapsulation efficiency of plasmid DNA.

Yet another alternative to polyelectrolyte complexation is to incorporate plasmid DNA into microemulsions. A microemulsion is a stable biphasic mixture of two immiscible liquids stabilized by a surfactant and usually a co-surfactant. Microemulsions are thermodynamically stable, isotropically clear, form without excessive mixing, and have dispersed droplets in the range of 5 nm to 100 nm diameter. Microemulsions have been proposed as drug delivery systems to enhance the absorption of drugs across biological membranes (Bhargava et al. 1987; Ho et al. 1996; Constantinides, 1995). Although microemulsions have advantages as delivery systems, they do have important limitations. For example, the dispersed droplets are a liquid and are not stable in biological fluids. Thus, microemulsions are not effective in delivering drugs intracellularly or targeting drugs to different cells in the body.

A significant advancement in the field of non-viral gene delivery would be made if one could avoid the problems associated with polyelectrolyte complexation and instead combine the unique advantages of solid nanoparticles and microemulsions into one pharmaceutically engineered gene delivery system.

Finally, there have been a handful of reports pertaining to the use of microemulsions to make nanoparticles (Li et al., 1999; Cavalli et al., 1999; Bocca et al., 1998; Tojo et al., 1998; Munshi et al., 1997; Ruys et al., 1999). These reports have primarily dealt with the preparation of water-in-oil (hydrocarbon) microemulsions (Lade et al., 2000; Song et al., 2000; Porta et al., 1999) whereby nanoparticles are formed in the water phase by the use of photochemistry (Agostiano et al., 2000), γ-rays (Xiangling et al., 1999), or electrochemistry (Tang et al., 2000) to induce crosslinking, polymerization (Fang et al., 2000; Capek, 1999; Meier, 1999) and/or complexation of the appropriate agents in the water phase. The great majority of these reports do not use pharmaceutically acceptable materials or methods of preparation that would be suitable for scale-up and preparation of nanoparticles containing drugs, magnets, or sensors that are intended for use in humans.

U.S. Pat. No. 4,826,689 to Violanto, discloses methods of making uniformly sized particles of less than 10 microns from water-insoluble drugs by precipitation. Although Violanto discloses a method of making drug particles by precipitation, the patent does not disclose alcohol-in-fluorocarbon microemulsions, liquid hydrocarbon-in-fluorocarbon microemulsions, or liquid hydrocarbon-in-Water microemulsions as precursors to prepare solid nanoparticles containing drug.

U.S. Pat. No. 4,997,599 to Steiner, discloses the preparation of cellulose acetate microspheres having a size of less than 1 micron to a maximum of 1000 microns by spraying a polymer solution through a nozzle. Although Steiner discloses the use of a film-forming cellulose polymer, the patent does not disclose alcohol-in-fluorocarbon microemulsions, liquid hydrocarbon-in-fluorocarbon microemulsions, or liquid hydrocarbon-in-water microemulsions as precursors to prepare solid nanoparticles containing drug.

U.S. Pat. No. 5,049,322 to Devissaguet discloses a process of preparing a colloidal system containing nanocapsules of less than about 500 nanometers. The patent reports that the colloidal system of nanocapsules forms practically instantaneously with gentle agitation. The wall of the nanoparticles is reported to be preferably formed of a film forming polymer, e.g., cellulose, and the core may be a biologically active substance. Although the patent describes nano-sized products, the patent does not disclose alcohol-in-fluorocarbon microemulsions, liquid hydrocarbon-in-fluorocarbon microemulsions, or liquid hydrocarbon-in-water microemulsions as precursors to prepare solid nanoparticles containing drug.

U.S. Pat. No. 5,500,224 to Vranckx describes pharmaceutical compositions containing nanocapsules. The nanocapsules are prepared by adding an aqueous solution containing an active ingredient to an oil to form a water-in-oil emulsion and removing the nanocapsules having a size of less than 500 nanometers. Although the patent describes nano-sized products, the patent does not disclose alcohol-in-fluorocarbon microemulsions, liquid hydrocarbon-in-fluorocarbon microemulsions, or liquid hydrocarbon-in-water microemulsions as precursors to prepare solid nanoparticles containing drug.

U.S. Pat. No. 5,733,526 to Trevino discloses hydrocarbon oil/fluorochemical preparations which may be used for the administration of bioactive agents. It is reported that the hydrocarbon oil, e.g., paraffin or vegetable oil, is preferably dispersed in a continuous fluorochemical phase. In an embodiment, the patent discloses a hydrocarbon oil-fluorochemical disperse phase in a continuous polar liquid. Trevino does not appear to disclose alcohol-in-fluorocarbon microemulsions, liquid hydrocarbon-in-fluorocarbon microemulsions, or liquid hydrocarbon-in-water microemulsions wherein the dispersed alcohol or liquid hydrocarbon phases contain a film-forming substance dissolved or dispersed therein. Further, the patent does not disclose the use of such microemulsions to prepare solid nanoparticles containing drug.

U.S. Pat. No. 5,250,236 by Gasco describes the use of solid lipid microspheres that are formed by diluting one volume of the mixture of molten lipid substance, water, surfactant and possibly a co-surfactant to 100 volumes of cold water. Gasco teaches the preparation of microspheres smaller than one micrometer and in particular between 50–800 nanometers, and preferably between 100 and 400 nanometers. Gasco also teaches the preparation of microspheres wherein said solid lipid microspheres may contain a pharmacologically active substance, such as a drug. Gasco does not teach the use of nanoparticles made from oil-in-water microemulsion precursors wherein said nanoparticles containing drugs are formed directly by cooling the oil-in-water microemulsion with no dilution of the most useful system.

Conventional microemulsions are water-in-oil type, and use various methods of curing the nanoparticles (i.e., crosslinking, polymerization, radiation, and so on). There is a need in the art to provide a non water-in-oil type microemulsions using curing methods specific to those non water-in-oil microemulsions, such as by cooling and evaporation or by the addition of a solvent, to prepare solid nanoparticles containing drug or other molecules of interest. An additional advantage of this invention over prior art is that the described nanoparticle systems can be engineered rapidly, reproducibly, and cost-effectively from the microemulsion precursors in a one-step process and contained in one manufacturing vessel, vial, or container.

SUMMARY OF THE INVENTION

The present invention has met the hereinbefore described need.

The present application discloses a method for incorporating a molecule of interest into microemulsion precursors and subsequently engineering stable solid nanoparticles (about 5–300 nm) containing the molecule of interest from the microemulsion precursor. The molecule of interest may be a drug molecule (such as plasmid DNA, a peptide, a protein, a small drug molecule, a food, a magnet or a sensor molecule). The molecule of interest may be physically contained in the nanoparticle or adsorbed onto the surface of the nanoparticle. The microemulsion precursors may be either an ethanol-in-fluorocarbon microemulsion, a liquid hydrocarbon-in-fluorocarbon microemulsion, or a liquid hydrocarbon-in-water microemulsion wherein film-forming substance is initially contained in the dispersed phase (ethanol or liquid hydrocarbon). Solid nanoparticles with the entrapped molecule of interest are made from the microemulsion precursors by a simple curing process. For all processes, the film-forming substance cures to form solid nanoparticles containing the molecule of interest. The present application also discloses characterizing the solid nanoparticles (i.e., size, surface charge and porosity, drug release and stability) and demonstrates that the solid nanoparticles are stable in biological fluids. The present application also discloses incorporating a targeting ligand such as asialofetuin or mannan onto the surface of the solid nanoparticles for targeting of the solid nanoparticles to specific cells of the body such as liver hepatocytes, macrophages, or dendritic cells. The present application also discloses methods to use solid nanoparticles to delivery macromolecules such as plasmid DNA more efficiently in-vivo to result in more robust immune responses.

These and other objects of the invention will be more fully understood from the following description of the invention, the referenced drawings attached hereto and the claims appended hereto.

BRIEF DESCRIPTION OF THE DRAWINGS

The present invention will become more fully understood from the detailed description given herein below, and the accompanying drawings which are given by way of illustration only, and thus are not limitative of the present invention.

Mice were immunized with 10 μg pDNA on day 0, 7, and 14 by subcutaneous administration of 'naked' pDNA, mannan-coated nanoparticles with pDNA, nanoparticles with pDNA, or mannan with free pDNA. Results are expressed as the mean IL-2 levels from pooled splenocytes harvested on day 28.

Figure 20:
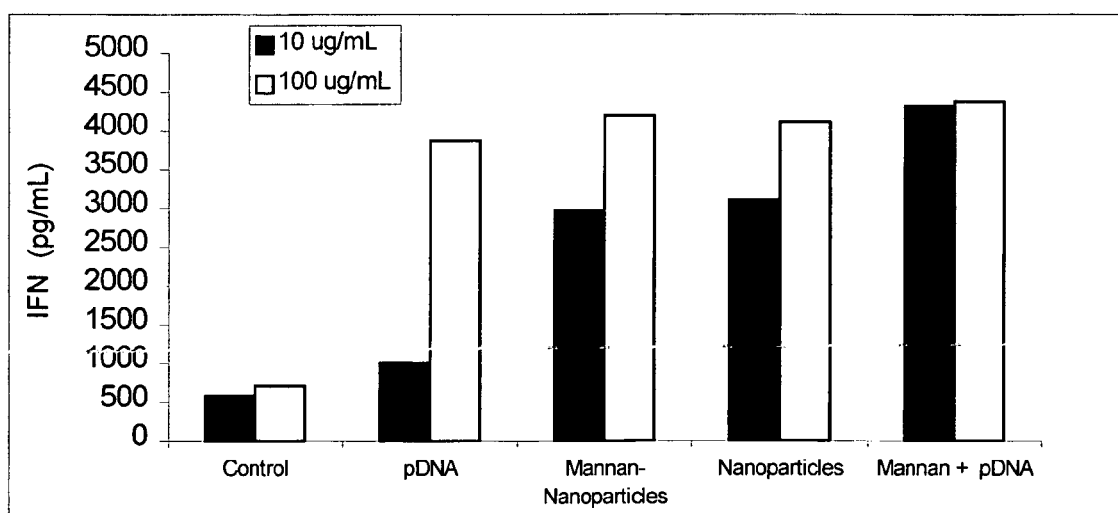

FIG. 20 Secretion of Interferon-γ (INF-γ) from isolated splenocytes ($1\times10^6$ cells) from immunized Balb/C mice after in-vitro exposure to β-galactosidase protein for 60 hours at a concentration of either 10 μg/mL or 100 μg/mL. Mice were immunized with 10 μg pDNA on day 0, 7, and 14 by subcutaneous administration of 'naked' pDNA, mannan-coated nanoparticles with pDNA, nanoparticles with pDNA, or mannan with free pDNA. Results are expressed as the mean INF-γ levels from pooled splenocytes harvested on day 28.

Figure 21:
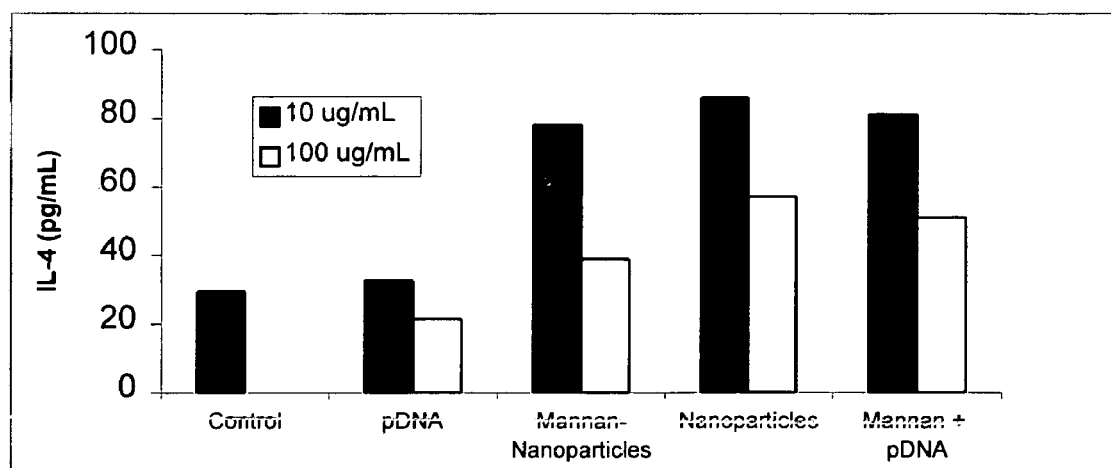

FIG. 21 Secretion of Interleukin-4 (IL-4) from isolated splenocytes ($1\times10^6$ cells) from immunized Balb/C mice after in-vitro exposure to β-galactosidase protein for 60 hours at a concentration of either 10 μg/mL or 100 μg/mL. Mice were immunized with 10 μg pDNA on day 0, 7, and 14 by subcutaneous administration of 'naked' pDNA, mannan-coated nanoparticles with pDNA, nanoparticles with pDNA, or mannan with free pDNA. Results are expressed as the mean IL-4 levels from pooled splenocytes harvested on day 28.

Figure 22:
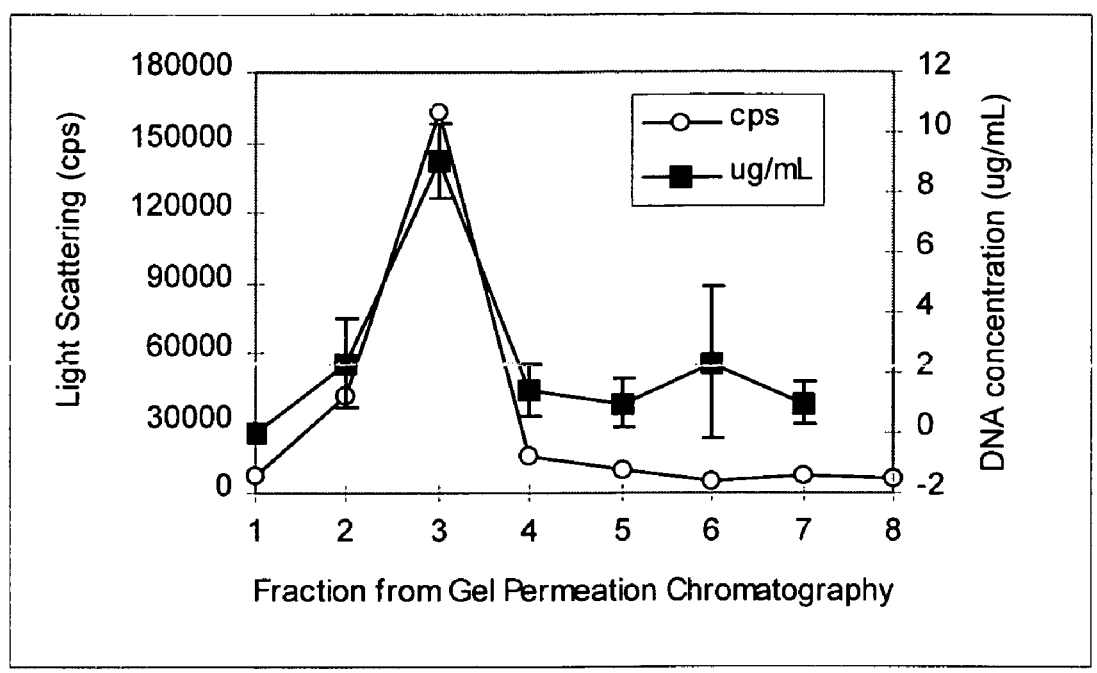

FIG. 22 Gel Permeation Chromatography (GPC) elution of cured emulsifying wax nanoparticles containing fluorescein-labelled plasmid DNA. See Example 18 for more details.

Figure 23:
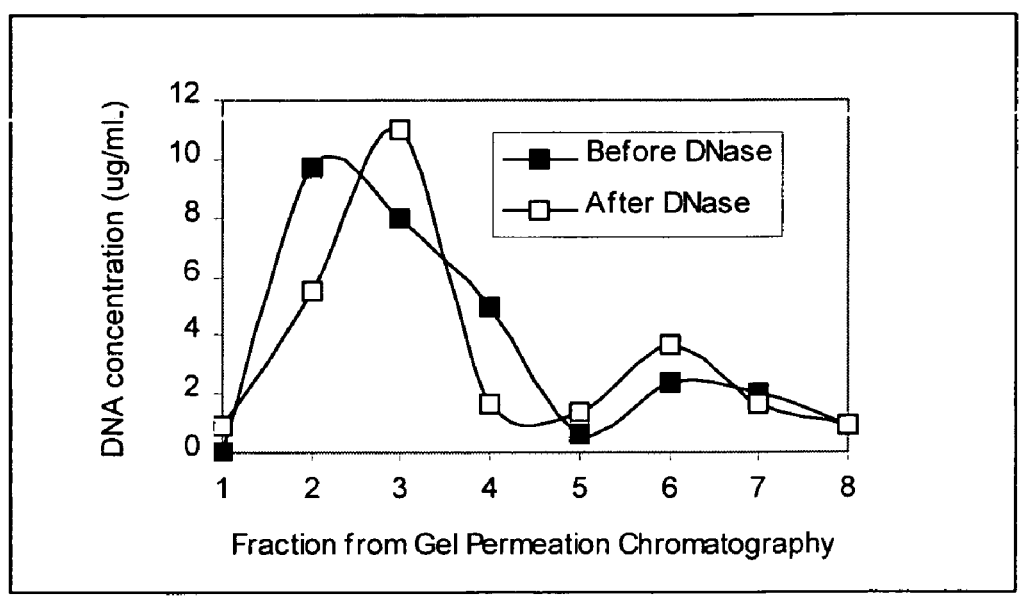

FIG. 23 Gel Permeation Chromatography (GPC) elution of cured emulsifying wax nanoparticles containing fluorescein-labelled plasmid DNA before and after DNase I nuclease treatment. See Example 18 for more details.

DETAILED DESCRIPTION OF THE INVENTION

The growing interest in nanotechnology has also resulted in the use of microemulsions as precursors or templates to form nanoparticles within the small dispersed droplets (Li et al., 1999; Cavalli et al., 1999; Bocca et al., 1998; Tojo et al., 1998; Munshi et al., 1996; Ruys et al., 1999). These reports have primarily dealt with the preparation of water-in-oil microemulsions (Lade et al. 2000; Song et al., 2000; Porta et al., 1999) whereby nanoparticles are formed in the water phase by the use of photochemistry (Agostiano et al., 2000), γ-rays (Xiangling et al., 1999), or electrochemistry (Tang et al., 2000) to induce crosslinking, polymerization (Fang et al., 2000; Capek, 1999; Meier; 1999) and/or complexation of the appropriate agents in the water phase.

This invention relates to microemulsions to be used as precursors for solid nanoparticles. The microemulsion precursors consist of either alcohol-in-fluorocarbon microemulsions, liquid hydrocarbon-in-fluorocarbon microemulsions, or liquid hydrocarbon-in-water microemulsions. The formed solid nanoparticles have diameters below 300 nanometers and can be made to contain various materials including drugs, magnets, and sensors. The solid nanoparticles can be made to target different cells in the body by the inclusion of a cell-specific targeting ligand. Methods of preparing the microemulsion precursors, and methods to cure solid nanoparticles are provided. Methods to administer useful nanoparticles to the human body are also described.

As used herein, certain terms may have the following defined meanings.

As used in the specification and claims, the singular form a, an, and the include plural references unless the context clearly dictates otherwise. For example, the term a nanoparticle may refer to one or more nanoparticles for use in the presently disclosed systems.

As used herein, the term "solubility" refers to the extent to which a solute is dissolved in a solvent. Solubility can be described in terms such as described in REMINGTON'S PHARMACEUTICAL SCIENCES ranging from very soluble (less than 1 part of solvent per 1 part of solute) to insoluble (more than 10,000 parts of solvent for 1 part of solute). The term "water-insoluble" refers to a substance or solute where more than 10,000 parts of water are needed to dissolve 1 part of solute.

The term "nanoparticle" refers to particles that have diameters below 1 micrometer in diameter that are comprised of primarily one solid phase. "Stable nanoparticles" remain largely unaffected by environmental factors such as temperature, pH, body fluids, or body tissues. However, solid nanoparticles may be designed to respond to these environmental factors in a controlled and predictable manner. The solid nanoparticles may contain, or have adsorbed to, many different materials for various pharmaceutical and engineering applications such as plasmid DNA for gene therapy and genetic vaccines, peptides and proteins or small drug molecules, magnetic substances for use as nanomagnets, lubricants, or chemical, thermal, or biological sensors. It is preferred that the nanoparticles have a diameter of less than about 300 nanometers and are present in the system at a concentration from about 0.1–30 mg/mL, even more preferably that the nanoparticles have a diameter of less than about 200 nanometers and are present in the system at a concentration from about 0.1–10 mg/mL.

As used herein, a "microemulsion" is a stable biphasic mixture of two immiscible liquids stabilized by a surfactant and usually a co-surfactant. Microemulsions are thermodynamically stable, isotropically clear, form spontaneously without excessive mixing, and have dispersed droplets in the range of about 5 nm to 140 nm. In contrast, emulsions are opaque mixtures of two immiscible liquids. Emulsions are thermodynamically unstable systems, and usually require the application of high-torque mechanical mixing or homogenization to produce dispersed droplets in the range of about 0.2 to 25 μm. Both microemulsions and emulsions can be made as water-in-oil or oil-in-water systems. Whether water-in-oil or oil-in-water systems will form is largely influenced by the properties of the surfactant. The use of surfactants that have hydrophilic-lipophilic balances (HLB) of about 3–6 tend to promote the formation of water-in-oil microemulsions while those with HLB values of about 8–18 tend to promote the formation of oil-in-water microemulsions.

Microemulsions were first described by Hoar and Schulman in 1943 after they observed that a medium chain alcohol could be added to an emulsion to produce a clear system within a defined 'window', now referred to as a microemulsion window. A unique physical aspect of microemulsions is the very low interfacial surface tension (γ) between the dispersed and continuous phases. In a microemulsion, the small size of the dispersed droplets present a very large interface. A thermodynamically stable microemulsion can only be made if the interfacial surface tension is low enough so that the positive interfacial energy (γA, where A equals the interfacial area) can be balanced by the negative free energy of mixing ($\Delta G_m$). The limiting γ value needed to produce a stable microemulsion with a dispersed droplet of 10 nm, for example, can be calculated as follows: $\Delta G_m =-$ $T\Delta S_m$ (where T is the temperature and the entropy of mixing $\Delta S_m$ is of the order of the Boltzman constant $\kappa_8$). Thus, $\kappa_B T = 4\pi r^2 \gamma$ and the limiting $\gamma$ value is calculated to be $\kappa^B T/4\pi r^2$ or 0.03 mN m$^{-1}$. Often, a co-surfactant is required in addition to the surfactant to achieve this limiting interfacial surface tension.

In addition to their unique properties as mentioned above, microemulsions have several key advantages for use as delivery systems intended for use in marketed pharmaceutical products, namely; i) increased solubility and stability of drugs incorporated into the dispersed phase, ii) increased absorption of drugs across biological membranes, iii) ease and economy of scale-up (since expensive mixing equipment is often not needed), and iv) rapid assessment of the physical stability of the microemulsion (due to the inherent clarity of the system). For example, oil-in-water microemulsions have been used to increase the solubility of lipophilic drugs into formulations that are primarily aqueous-based (Constantinides, 1995). Both oil-in-water and water-in-oil microemulsions have been also been shown to enhance the oral bioavailability of drugs including peptides (Bhargava et al. 1987; Ho et al. 1996; Constantinides, 1995).

Although microemulsions have many potential advantages they do have potential limitations, namely; a) they are complex systems and often require more development time, b) a large number of the proposed surfactants/co-surfactants are not pharmaceutically acceptable (Constantinides, 1995), c) the microemulsions are not stable in biological fluids due to phase inversion. Thus, the microemulsions themselves are not effective in delivering drugs intracellularly or targeting drugs to different cells in the body. The development of a microemulsion involves the very careful selection and titration of the dispersed phase, the continuous phase, the surfactant and the co-surfactant. Time consuming pseudo-phase ternary diagrams involving the preparation of a large number of samples must be generated to find the existence of the 'microemulsion window', if any (Attwood, 1994). In general, a water-in-oil microemulsion is typically much easier to prepare than an oil-in-water microemulsion. The former system is useful for formulating water-soluble peptides and proteins to increase their stability and absorption while the latter system is preferred for formulating drugs with little or no aqueous solubility.

As used herein, a "surfactant" refers to a surface-active agent, including substances commonly referred to as wetting agents, detergents, dispersing agents, or emulsifying agents. For the purposes of this invention, it is preferred that the surfactant has an HLB value of about 6–20, and most preferred that the surfactant has an HLB value of about 8–18. It is preferred, but not required, that the surfactant, either non-ionic, ionic, or cationic, is selected from the following groups; polyoxyethylene alkyl ethers, polyoxyethylene sorbitan fatty acid esters, polyoxyethylene stearates, or fatty alcohols or their derivatives, hexadecyltrimethylammonium bromide, or combinations thereof. A "co-surfactant" refers to a surface-active agent, including substances commonly referred to as wetting agents, detergents, dispersing agents, or emulsifying agents. It is preferred, but not required, that the co-surfactant is selected from the following groups; polyoxyethylene alkyl ethers, polyoxyethylene sorbitan fatty acid esters, polyoxyethylene stearates, or fatty alcohols or their derivatives, hexadecyltrimethylammonium bromide, or combinations thereof. It is also preferred that the total concentration of surfactant and/or co-surfactant present in both the oil-in-water microemulsion precursor and the cured nanoparticles system is in the range of about 1–5000 mM, more preferably in the range of about 1–1000 mM, and most preferably in the range of about 1–300 mM.

As used herein, an "ethanol-in-fluorocarbonmicroemulsion" is a stable biphasic mixture of ethanol dispersed in a fluorocarbon wherein the ethanol droplets have diameters ranging from about 5 nm to about 500 nm, preferably from about 5 nm to about 250 nm, and most preferably from about 5 mm to about 100 nm.

As used herein, a "liquid hydrocarbon-in-fluorocarbon microemulsion" is a stable biphasic mixture of a liquid (melted) hydrocarbon dispersed in a fluorocarbon wherein the liquid hydrocarbon droplets have diameters ranging from 5 nm to 500 nm, preferably from 5 mm to 250 nm, and most preferably from 5 nm to 100 nm. A "liquid hydrocarbon" is any material that is a solid below body temperature (35–38° C.), but a liquid at temperatures greater than body temperature.

As used herein, a "liquid hydrocarbon-in-water microemulsion" is a stable biphasic mixture of a liquid (melted) hydrocarbon dispersed in water wherein the liquid hydrocarbon droplets have diameters ranging from about 5 nm to about 500 nm, preferably from about 5 nm to about 250 nm, and most preferably from about 5 nm to about 100 nm.

As used herein, a "film-forming substance" may be any pharmaceutical material that is soluble or dispersible in the dispersed phase, or actually be the dispersed phase when melted to a liquid, and that can be cured by a curing process to form a solid membrane suitable for the delivery of drugs by different routes of administration.

As used herein, the term "nanoparticle matrix material" refers to those materials that can form both the shell and majority of the weight composition of the said nanoparticle. Two types of matrix materials are envisioned, both serving as the oil-phase in the oil-in-water microemulsion precursor. The first matrix materials are those materials that are amphipathic in nature (having both hydrophilic and hydrophobic moieties), are primarily water-insoluble, and that melt above room temperature in the range of about 35–100° C., more preferably in the range of about 35–80° C., and most preferably in the range of about 35° C.–65° C. It is envisioned that these materials can be any substance meeting the above criteria and that are a wax, lipid, polymeric surfactant, or combinations thereof. It is most preferred, but not absolutely required, that these materials are selected from the following: emulsifying wax, polyoxyethylene sorbitan fatty acid esters, polyoxyethylene alkyl ethers, polyoxyethylene stearates, phospholipids, fatty acids or fatty alcohols or their derivatives, or combinations thereof. It is preferred that the nanoparticle matrix material is present in both the microemulsion precursor and cured nanoparticles at a concentration of about 0.1–30 mg/mL, and more preferably at a concentration of about 0.1–10 mg/mL.

As used herein, a "curing process" is the process whereby the film-forming substance residing in the dispersed phase of the stable microemulsion precursor is cured to form solid nanoparticles containing entrapped drug molecules. In particular, the curing process may consist of evaporating the dispersed liquid to precipitate the film-forming substance, adding water or some combination of water to precipitate the film-forming substance, or by cooling the liquid (melted) dispersed phase to solidify the film-forming substance.

As used herein, a "solid nanoparticles" are particles below 1 micron in diameter that are comprised of primarily one solid phase. "Stable solid nanoparticles" remain largely unaffected by environmental factors such as temperature, pH, body fluids, or body tissues. However, solid nanoparticles may be designed to respond to these environmental factors in a controlled and predictable manner to deliver their contents in a controlled and predictable manner. The solid nanoparticulate systems may contain (by entrapment or adsorption) many different materials for various pharmaceutical and engineering applications such as plasmid DNA for gene therapy and genetic vaccines, peptides and proteins or small drug molecules, magnetic substances for use as nanomagnets, or chemical, thermal, or biological sensors for use as nanosensors.

As used herein, the term "permanently suspended" refers to nanoparticles, engineered from said microemulsion precursors, that remain suspended in aqueous media such as water or buffer for at least one month at room temperature and that cannot be settled by ultracentrifugation treatment at about 50,000 cpm for about 5 minutes.

As used herein, the term "ligand" refers to those substances that can be recognized and bind to a specific molecule, a cell-receptor, an antibody, an anti-antibody, or combinations thereof. It is preferred that the ligand be comprised of carbohydrates or amino acids or combinations thereof. It is most preferred that the ligand be a monoclonal or polyclonal antibody. The ligand may be attached onto said nanoparticles by any number of processes including, but not limited to, covalent attachment, ionic interaction, hydrophobic interaction, and hydrogen bonding. It is also envisioned that the ligand may be chemically modified to enhance the attachment of said ligand to said nanoparticle to either increase the efficiency of detection or selectively detecting one or more radioactive molecules from other molecules. Most preferred in the invention are those ligands specific for, 1) tumor cells, such as folate and antibodies, 2) hepatocytes, such as asialofetuin and other galactose containing ligands, and 3) macrophages and dendritic cells, such as mannan, mannose, or synthetic or natural peptides.

Microemulsion Precursors: To overcome the problems associated with polyelectrolyte complexation and conventional solid nanoparticles and to exploit the benefits of microemulsions, we have developed a process to pharmaceutically engineer solid nanoparticles containing drugs that do not require the use of rigorous processes. The strategy involves the spontaneous formation of a microemulsion precursors wherein the microemulsion is subsequently treated to cure solid nanoparticles between about 5–300 nm. Curing may be completed either by adding water to the microemulsion, applying heat to remove the solvent, or most preferably, by simple cooling of the microemulsion. For the purposes of this invention, three microemulsion precursors are preferred, 1) an ethanol-in-fluorocarbon microemulsion, also referred to as E/F, 2) a liquid hydrocarbon-in-fluorocarbon microemulsion, also referred to as O/F, and 3) a liquid hydrocarbon-in water microemulsion, also referred to as O/W.

Ethanol-in-fluorocarbon microemulsion containing film-forming polymers: Ethyl cellulose is an inert, biocompatible polymer available in a variety of molecular weights. Ethyl cellulose polymers, dissolved in ethanol, instantaneously precipitate when exposed to water. When ethanol solutions containing ethyl cellulose and a drug are applied to the skin or mucosal surfaces, the ethyl cellulose very quickly forms a strong film. This film functions as a reservoir for the controlled-release of drug. We hypothesized that if this ethanolic phase could be dispersed into a fluorocarbon phase and stabilized to form an E/F microemulsion, the dispersed ethanol droplets (about 5–140 nm) containing ethyl cellulose may constitute a "template" for solid nanoparticles when the E/F microemulsions were exposed to aqueous solutions or if the ethanol was removed by evaporation. If plasmid DNA was dissolved in the ethanol phase then it could be entrapped in the solid nanoparticles.

Fluorocarbons are carbon-based molecules with some or all of the hydrogen atoms replaced with fluorine. They have unique properties including chemical and biological inertness, low surface tension, high density, unique hydrophobicity, and the ability to dissolve large amounts of gases (Riess and Krafft, 1997). In the present application, perfluorooctyl bromide ($CF_3(CF_2)_6CF_2Br$; perflubron) is exemplified as the fluorocarbon because of its well-documented safety profile and its growing use in (micro)emulsion-based delivery systems for drugs and oxygen (Riess and Krafft, 1997; Lattes et al., 1997; Cornelus et al., 1994; Gauger et al., 1996). Importantly, for forming a microemulsion, ethanol is not miscible with perflubron but may be dispersed in perflubron using an appropriate surfactant. Thus, the use of E/F microemulsions and specifically the use of perflubron, have a number of advantages. The engineering of solid ethyl cellulose nanoparticles containing plasmid DNA following the rationale and concepts described above are not possible using traditional water-in-oil (W/O) or oil-in-water (O/W) microemulsions.

In addition to the ethyl cellulose and a molecule such as plasmid DNA, the ethanol droplets in the E/F microemulsion may contain a number of excipients including a small amount of water (only up to 20% v/v), pore-forming polymers to control the release of the plasmid DNA, endosomolytic agents to disrupt endosomal membranes, nuclear targeting agents to target plasmid to the nuclear membrane, and other excipients as needed. This E/F microemulsion precursor strategy has advantages since; i) all ingredients are potentially biocompatible and those that may not be are removed when the solid nanoparticles are cured and isolated, ii) perflubron and the surfactant and co-surfactant may be recycled, iii) well-defined and uniform solid nanoparticles (about 5–300 nm) may be reproducibly made without the use of high-torque mechanical mixing, microfluidization, or homogenization, iv) the formed solid nanoparticles may have superior in-vivo stability, and v) cell-specific targeting ligands can easily be incorporated into the system (during or after the engineering process). These solid nanoparticles may have applications in the areas of non-viral gene delivery. For example, due to their small size and stability, these nanoparticles may have greater access to tissues and cells than larger, less stable plasmid DNA polyelectrolyte complexes (i.e., liver hepatocytes, tumor cells, or antigen-presenting cells, etc.).

Cell-Specific Targeting to the Liver. Since the discovery of the hepatic asialoglycoprotein receptor in the early 1970s there have been a plethora of attempts to target molecules, such as genes, specifically to hepatocytes. The asialoglycoprotein receptor on hepatocytes functions, in part, to remove circulating glycoproteins from the blood. This aspect of the receptor has led to the design and testing of a number of targeted systems primarily using different natural, synthetic, or semi-synthetic glycosylated proteins, polymers, or lipids (Meijer et al. 1995). The carrier systems described are comprised of conventional nanoparticles, liposomes, conjugated soluble polymers, or viruses. It is generally thought that the targeted systems must have three properties to specifically target hepatocytes. First, the systems must be less than about 100 nm in size, and preferably less than about 50 nm. Particles with diameters greater than about 100 nm cannot traverse the fenestrae (pores) in the endothelial lining to gain access to the hepatocytes (Schlepper-Schafer et al. 1986; Mandeville et al., 1997). Second, the systems must be stable in the blood. Unstable particles that aggregate will become too large to diffuse through the fenestrae. For example, although hepatocyte-targeted polyelectrolyte complexes of poly-L-lysine and plasmid DNA have been produced in the size range of about 50–100 nm, these complexes aggregate even in physiological saline alone (Wu and Wu, 1988; Kwoh et al. 1999; Plank et al., 1992). Third, the systems generally have to employ a clustering of the glycosylated ligands. For example, tri-antennary asialoglycoproteins have much greater affinity for the receptor than do bi- and mono-antennary asialoglycoproteins (Wadhwa and Rice, 1995).

In this application, a unique system comprising stable ethyl cellulose nanoparticles (about 5–50 nm) containing a molecule of interest, such as plasmid DNA and asialofetuin as the hepatocyte-specific ligand. Asialofetuin (45,450 g/mol) is a natural glycopeptide having three major glycosylation sites comprised of about two-thirds tri-antennary and one-third bi-antennary functionalities. Asialofetuin has been used previously to increase delivery of substances to the liver including, liposomes (Sliedregt et al. 1999; Wu et al. 1998), contrast agents (Mandeville et al. 1997), plasmid DNA (Plank et al. 1992), gold particles (Schlepper-Schafer et al. 1986), and several other drugs (Wadhwa and Rice, 1995; Meijer et al. 1995). Importantly, we are not limited to the use of ethyl cellulose as the film-forming material. In fact, any water insoluble material including lipids, peptides, or other polymers that have solubility in ethanolic solutions may be utilized as the film-forming material.

It has been demonstrated that stable ethanol-in-perflubron microemulsions could be formed using at least four different fluorosurfactants. A microemulsion using pentadecafluorooctanoicacid (PDFOA) in a ratio of 70:30 (w/w) perflubron/PDFOA was able to solubilize up to 37.2% ethanol (w/w). In this same microemulsion, a film-forming polymer could be incorporated into the system by adding ethyl cellulose dissolved in ethanol without altering the existence of the microemulsion window. For E/F microemulsions made without a co-surfactant or ethyl cellulose, the average droplet size of ethanol was 34.9 nm. The actual amount of PDFOA needed to coat the surface of all ethanol droplets in this microemulsion was within 3% of the theoretical amount needed and supported the formation of an E/F microemulsion. E/F microemulsions incorporating about 5% ethyl cellulose in the ethanol phase had an unexpectedly small droplet size of only about 8 nm suggesting unknown effects of the ethyl cellulose.

Figure 1:
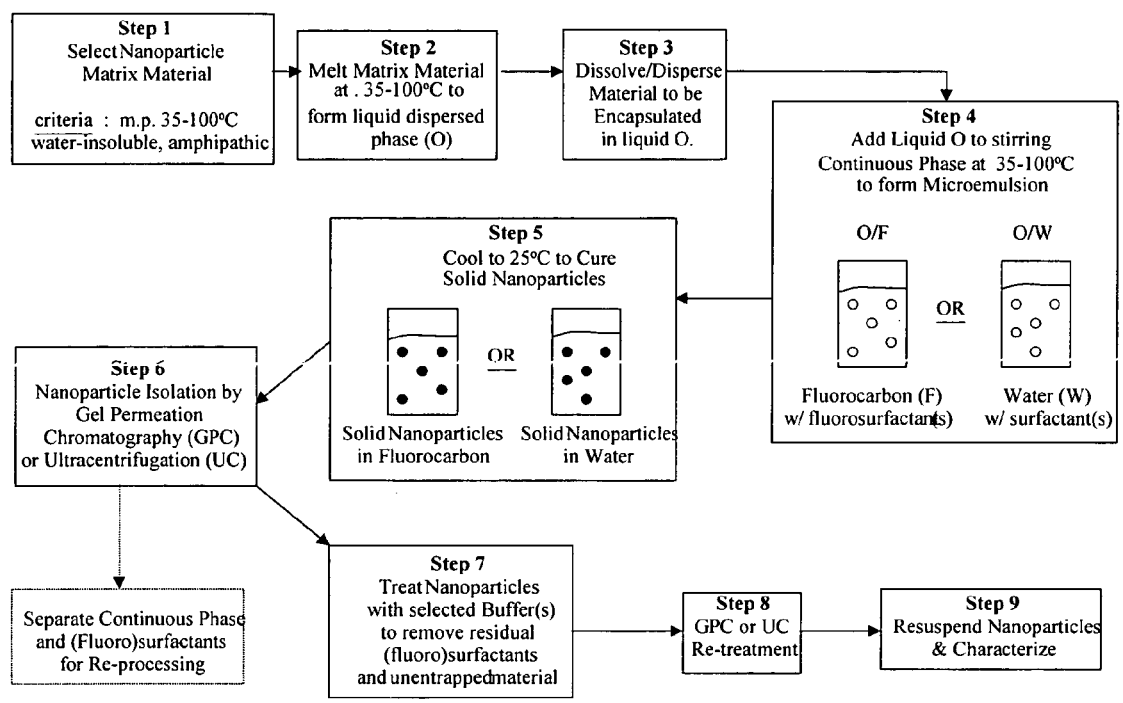
FIG. 1 A diagram of a method to engineer solid nanoparticles from microemulsion precursors.
Figure 2:
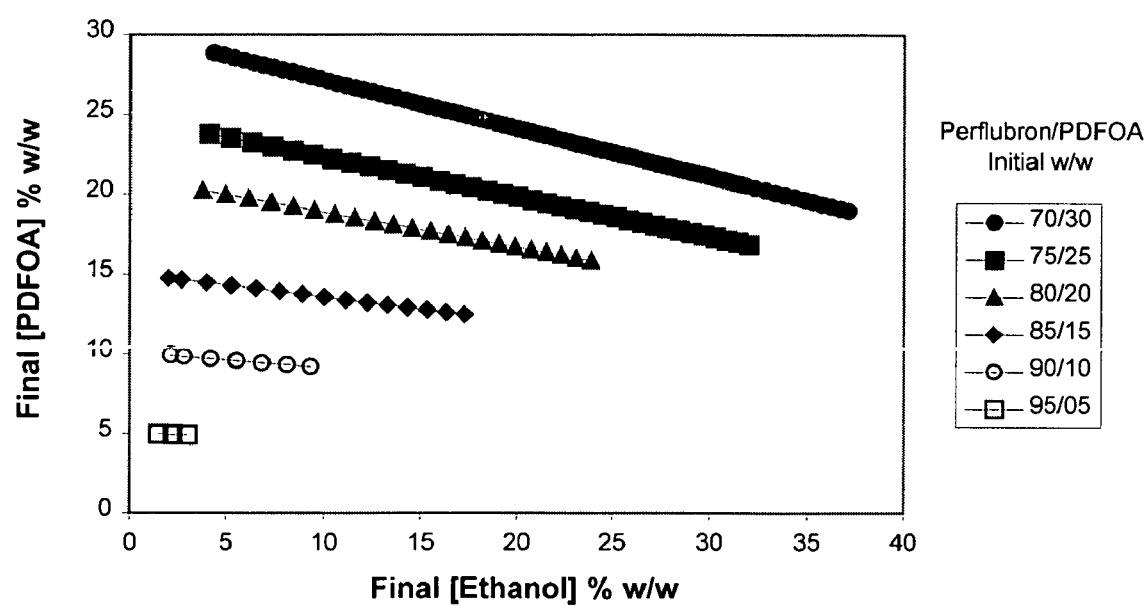
FIG. 2 Solubilized ethanol in ethanol-in-fluorocarbon (E/F) microemulsions as a function of fluorosurfactant (PD-FOA, pentadecafluorooctanoicacid) content.

Liquid hydrocarbon-in-water microemulsions: In another aspect of the invention, liquid matrix microemulsions are made. The basic concept of liquid matrix microemulsion precursors is shown in FIG. 2. The concept avoids the use of an ethanol dispersed phase to solubilize the film-forming polymer. Instead, the nanoparticle matrix material alone is melted and then dispersed in a heated continuous phase with an appropriate surfactant and/or co-surfactant to form a heated microemulsion precursor at the same temperature. The heated microemulsion precursor is then simply cooled to room temperature to cure solid nanoparticles. The nanoparticles are then isolated and purified as described in FIG. 2.

The liquid matrix microemulsion precursor method may have a number of advantages over the E/F microemulsion method namely, 1) no additional materials such as water have to be added to the formed microemulsion to cure the solid nanoparticles, the microemulsion precursor is simply cooled, 2) high entrapment efficiencies may be achieved since the dispersed droplets are composed entirely of the matrix material. 3) the dispersed phase is not limited only to the use of ethanol, which is used in the E/F microemulsions, but to any matrix material meeting the criteria and from which a stable microemulsion precursor can be made, and 4) no organic solvents are needed to form the microemulsion precursors.

Gadolinium and Neutron Capture Therapy of Tumors: Gadolinium, a rare-earth metal, has been proposed as an alternative to boron for neutron capture therapy of tumors. In contrast to Boron-10, which emits short-range alpha-particles when exposed to thermal neutron irradiation, Gadolinium-157 emits gamma rays and Auger electrons. Consequently, Gadolinium-157 neutron capture therapy may increase the probability of hitting a larger number of tumor cells with long-range photons (>100 µm) and high-energy electrons. Gadolinium-157 also has a very large neutron capture cross section of 255,000 barns which is almost 70-fold greater than Boron-10. Thus, much shorter neutron irradiation times are needed for Gadolinium-157 neutron capture therapy than for Boron-10 neutron capture therapy. The intratumoral administration of delivery systems for gadolinium such as gadolinium/chitosan complexes, and emulsions and microspheres containing gadolinium have recently been reported. (Tokumitsu et al. 1999; Tokumitsu et al. 2000; Miyamoto et al. 1999; Jono et al. 1999). In most cases, these particulate delivery systems for gadolinium were quite large (i.e., 400 nm to several microns in size). For targeting solid tumors, it preferred that the nanoparticles containing Gadolinium, or its derivatives or complexes thereof, have a particle size below about 300 nm, and more preferably below about 200 nm, and most preferably below about 100 nm.

Genetic Immunization: Genetic immunization has emerged as one of the most promising applications of non-viral gene therapy (Liu et al. 1995, Ulmer et al. 1996, Levine et al. 1997). The potential advantages of DNA vaccines over conventional vaccines include, i) the high stability of plasmid DNA, ii) low manufacturing costs, iii) lack of infection risk associated with attenuated viral vaccines, iv) the capacity to target multiple antigens on one plasmid, and v) the ability to elicit both humoral and cellular immune responses (Mumper et al. 2001). The ability of genetic vaccines to elicit cellular immunity is of great importance to those working in the vaccine field. Vaccines that generate cellular immunity mediated by the generation of cytotoxic T lymphocyte (CTL) responses have been called the "the immunologist's grail" (Liu 1997). These vaccines may be of prime importance for protection from intracellular viral infections and as immunotherapies for cancer. Immunization with 'naked' plasmid DNA has been found to induce strong T helper cell type 1 ($T_H1$) immune responses (Robinson and Torres, 1997) as evidenced by the protection of cytokines such as interleukin-2 (IL-2) and interferon-γ (INF-γ). In contrast, subunit, or protein-based, vaccines tend to induce T helper cell type 2 ($T_H2$) immune responses as evidenced by the protection of cytokines such as interleukin-4 (IL-4) and interleukin-10 (IL-10). Importantly, $T_H1$ cells aid in the regulation of cellular immunity. In contrast, $T_H2$ cells aid in the production of antibodies such as IgA and IgE. Improved immunization methods to induce cellular immunity and $T_H1$ type immune responses are needed in the field.

Until recently, intramuscular (i.m.) injection was the primary route of administration for DNA vaccines. The i.m. route has been shown to elicit protective and therapeutic immune responses in many animal models. However, the low bioavailability of plasmid DNA in the muscle coupled with the redundant nature of antigen transfer by muscle cells clearly raised the issue about the rationale of this route (Ulmer et al. 1996, Corr et al. 1996, Huang et al. 1994, Doe et al. 1996, Corr et al. 1999, Torres et al. 1997). Also, there has been no conclusive clinical data suggesting that the i.m. route is viable in humans. As an alternative to intramuscular administration of plasmid DNA, researchers have investigated targeting plasmid DNA to the skin using intradermal needle injection, needle-free jet injection devices, or the gene gun. Intradermal needle injections of plasmid DNA into the skin has been shown to be more effective than intramuscular injection in several animal species in eliciting immune responses (Braun et al. 1998, Gerdts et al. 1997, Van Rooij et al. 1998, Van Drunen et al., 1998). Further, several preclinical animals studies have reported on the use of needle-free jet injection devices and the gene gun to administer plasmid DNA (Tang et al. 1992, Fynan et al. 1993, Degano et al. 1998, Pertmer et al. 1995, Yoshida et al. 2000). Recent clinical trials using the gene gun to administer plasmid DNA-based vaccines to the skin epidermis in humans showed that this technology may be an effective clinical vaccine modality for the treatment or prevention of hepatitis B or malaria. Although these preclinical and clinical results are promising, it is not clear whether these technologies will translate into safe, commercially available and affordable vaccines.

The growing body of evidence that pointed to the significance of the role of Langerhan's cells in the epidermis prompted researchers to consider alternatives to gene gun and jet injection to target plasmid to this site. Topical delivery of formulated plasmid in the form of a patch, cream, or gel may provide many advantages in terms of cost and patient compliance (Shi et al. 1999, Fan et al. 1999, Tang et al. 1997). Shi et al. demonstrated the feasibility of topical genetic immunization in mice by applying plasmid DNA complexed to cationic liposomes to chemically (Nair)-treated skin for 18 h (Shi et al. 1999). Antigen expression at the site of administration was extremely low and virtually unquantifiable in the skin 18 h after topical administration and the immune responses were 100-fold lower than those for mice immunized with 50 μg of 'naked' plasmid injected into the muscle. Fan et al. demonstrated that the immune response to expressed β-galactosidase in mice were comparable at four weeks after both topical and intramuscular administration of 100 μg 'naked' plasmid and 100 μg plasmid complexed with cationic liposomes (Fan et al. 1999). It was further demonstrated, by skin graft transplantation studies, that the presence of normal hair follicles was required to elicit a humoral immune response to expressed antigen. Taken together, the studies by Shi et al. and Fan et al. demonstrated the feasibility of topical genetic immunization. However, these studies also indicated the need for more effective topical delivery systems that would allow for much lower doses of plasmid DNA to skin not pre-treated with chemicals.

Singh et al. have demonstrated enhanced immune responses in mice over 'naked' plasmid DNA after intramuscular injection of pDNA-coated cationic polylactic acid-co-glycolic acid (PLGA) microspheres (Singh et al. 2000). These PLGA microspheres were made cationic by the inclusion of cationic surfactants such as hexadecyltrimethylammonium bromide (CTAB). Singh et al. also investigated immune responses to p55 Gag protein using pDNA-coated on different sizes of cationic PLGA microspheres (300 nm, 1 μm, 30 μm). Singh et al. found a direct correlation between microsphere size and immune response wherein pDNA-coated PLGA/CTAB microspheres with a size of 300 nm led to the highest immune response after intramuscular injections (2×1 μg pDNA) of the formulations. Although these results were encouraging, the difficulty in preparing PLGA microspheres below 300 nm, the use of solvents such as methylene chloride, and the inclusion of cationic surfactants may be problematic for future clinical investigation. As a result, we sought to investigate the more facile preparation of smaller nanoparticles engineered from microemulsion precursors in a single vial that could then serve as a more pharmaceutically-acceptable template to coat or entrap pDNA.

Methods used to administer and evaluate genetic vaccines: For topical application, the hair covering the back of the mouse was shaved with clippers. The skin was wiped with an alcohol swab, allowed to air dry, and 100 μl of each formulation was dripped and subsequently rubbed with pipette tips onto the skin covering an area of about 2 cm². For intramuscular injection, the hair covering the back of the gastrocnemious muscle on both legs was shaved, wiped with an alcohol swab, and allowed to air dry. Fifty microliters of each formulation was injected into the gastrocnemious muscles on both legs. A typical immunization schedule is to dose the formulation at day 0, 7, and 14. At day 28, all mice were anesthetized using pentobarbital (i.p.) and blood was collected by cardiac puncture. The blood was transferred into a Vacutainer Collection Tube (Becton Dickinson). Serum was separated by centrifugation and stored at −20° C. until analyzed. The β-galactosidase specific sera IgG level were quantified by ELISA. Briefly, Costar high binding 96-well assay plates were coated with 8 μg/ml of β-galactosidase antigen overnight at −4° C. The plates were then blocked with 100 μl/well of 4% BSA/4% Normal Goat Serum (NGS) solution made in 10 mM PBS/Tween 20 (Scytek Laboratories; Logan, Utah) for 1 hr at 37° C. Mouse serum samples (50 μL/well; starting dilution of 20:100 in 4% BSA/4% NGS/PBS/Tween 20) were serially diluted and then incubated for 2 hr at 37° C. Afterward samples were washed with 10 mM PBS/Tween 20 buffer three times, and Anti-mouse IgG HRP F(ab')$_2$ fragment from sheep (diluted 1:2,000 in 1% BSA) was added (50 μL/well) and incubated for 1 hr at 37° C. Plates were washed three additional times with 10 mM PBS/Tween 20 buffer. One hundred microliters of tetramethybenzidine (TMB) solution reagent was added to each well and incubated at room temperature for 10 min followed by the addition of 50 μl 0.2 M of $H_2SO_4$. The O.D. of each sample was measured by using Universal Microplate Reader (Bio-Tek Instruments, Inc., Winooski, VM) at 450 nm. Purified monoclonal anti-β-galactosidase was used for the standard curve.

Secretion of various cytokines (IL-2, INF-γ, and IL-4) from splenocytes of immunized Balb/C mice was determined by isolating splenoctyes (1×10⁶ cells) and exposing to β-galactosidase protein for 60 hours at a concentration of either 10 μg/mL or 100 μg/mL. Mouse cytokine kits were purchased from Endogen, Inc. (Woburn, Mass.) and used as directed.

The following examples are offered by way illustration of the present invention, and not by way of limitation.

EXAMPLE 1

Plasmid DNA Solubility in Ethanol. For all studies, we utilized plasmid DNA that contains the cytomegalovirus (CMV) enhancer and promoter and the luciferase gene ligated into a pBluescript KS-derived backbone modified to contain the kanamycin resistance gene, Tn5 (derived from pNEO, Pharmacia, Piscataway, N.J.) and with the deletion of the f1 origin of replication. The plasmid DNA was obtained from GeneMedicine, Inc. (now Valentis, Inc.).

Solubility and stability of plasmid DNA in the ethanol phase is imperative in order to encapsulate large amounts of plasmid DNA in the solid ethyl cellulose nanoparticles. Fortunately, the exposure of plasmid DNA to ethanol/salt mixtures is a common technique to precipitate and purify plasmid DNA. A simple solubility experiment was performed to demonstrate that plasmid DNA remained soluble when aqueous solutions of plasmid DNA were diluted with 95% ethanol. To stirring plasmid DNA (1 mg in 1 mL of water) in a glass vial, ethanol was added in 25 μL aliquots (25 μL/minute) until the final solution was 95% ethanol (i.e., 19 mL ethanol plus 1 mL water). Our observation showed that plasmid DNA remained soluble in 95% ethanol. At this point, 15 μL of 5 M NaCl was added to the plasmid DNA in 95% ethanol. Plasmid DNA immediately precipitated into a large stringy precipitate. This experiment demonstrated that plasmid DNA may be solubilized in the ethanol dispersed phase for subsequent encapsulation in the ethyl cellulose nanoparticles. Although the final plasmid DNA concentration in this experiment was only 50 μg/mL, it is likely that the concentration can be increased considerably.

EXAMPLE 2

Selection of Fluorosurfactants. For initial testing as possible surfactants, we selected or synthesized a series of fluorinated surfactants as shown in Table 1. These fluorosurfactants have chemical moieties allowing for both association or solubility with the perflubron continuous phase (highly fluorinated chains) and association or solubility with the ethanol dispersed phase (polar head-groups).

TABLE 1

Fluorosurfactants Used in Preliminary Studies

| Fluorosurfactant | Structure |
| --- | --- |
| FSN-100 (Zonyl ®) | $F(CF_2CF_2)_{1-9}CH_2CH_2O(CH_2CH_2O)_{0-25}H$ |
| FSO-100 (Zonyl ®) | $F(CF_2CF_2)_{1-7}CH_2CH_2O(CH_2CH_2O)_{0-15}H$ |
| Pentadecafluorooctanoicacid | $CF_3(CF_2)_6COOH$ |
| D2 | Proprietary structure |
| Tridecafluoro-1-octanol(D3) | $CF_3(CF_2)_5(CH_2)_2OH$ |
| D4 | Proprietary structure |
| Tridecafluoroheptanoicacid (D5) | $CF_3(CF_2)_5COOH$ |
| Perfluorotetradecanoicacid (D6) | $CF_3(CF_2)_{12}COOH$ |
| Perfluorododecanoicacid (D7) | $CF_3(CF_2)_{10}COOH$ |
| Pentadecafluoromethyloctanoate(D8) | $CF_3(CF_2)_6COOCH_3$ |
| Octanoic acid (Control) | $CH_3(CH_2)_5CH_2COOH$ |

EXAMPLE 3

Pseudo-Phase Diagrams: Fluorosurfactant Screen. Studies focused on E/F microemulsions that allowed for maximum solubilization of ethanol. E/F microemulsion systems having higher ethanol content allow for increased concentration of plasmid DNA in the systems and ultimately the cured solid nanoparticles. To achieve maximum solubilization of ethanol, we constructed classical pseudo-phase diagrams for microemulsions (Bhargava et al., 1987) using a matrix screening approach for each fluorosurfactant candidate. Briefly, a small amount of ethanol was added to defined perflubron (X %)/(fluorosurfactant) (100-X %) mixtures in an attempt to solubilize ethanol and define the microemulsion window (i.e., portion of diagram that represents a clear system). A 0.5 g mixture of perflubron (X=70% to 95% w/w) and fluorosurfactant (5% to 30% w/w) was prepared in glass vials. While the mixture was stirring, ethanol was added in 5 μL (=4.1 μg ethanol) aliquots. The clarity (transparency) of the systems as a function of the percentages of the three phases was plotted in order to define the microemulsion window, if any. This screen was repeated for each of the fluorosurfactant candidates. The maximum amount of ethanol incorporated into a stable clear microemulsion for selected fluorosurfactantsis shown in Table 2.

TABLE 2

Incorporation of Ethanol in E/F Microemulsions Using Different Fluorosurfactants

| Fluorosurfactant | Final (Ethanol) % w/w Solubilized in Perflubron/Fluorosurfactant (70/3 w/w) |
| --- | --- |
| FSN-100 | 10.1 |
| FSO-100 | 18.8 |
| Pentadecafluorooctanoicacid (PDFOA) | 37.2 |
| D4 | 32.0 |
| Perfluorotetradecanoicacid (D6) | 66.6 |
| Perfluorododecanoicacid (D7) | 59.2 |

As expected, no E/F microemulsion could be formed with the octanoic acid control due to the fact that the molecule is not fluorinated. The microemulsions shown in Table 2 were clear and stable throughout the microemulsion window, except for the system made with D4. The use of D4 produced a slightly opaque system. The use of D6 and D7 resulted in microemulsions that apparently solubilized a high amount of ethanol in perflubron. However, it is very likely that these microemulsions were actually reverse perflubron-in-ethanol systems based on mathematical modeling of surfactant-coated ethanol or perflubron droplets (see examples of similar calculations shown later). Fluorosurfactants D2, D3, D5, and D8 were all soluble in perflubron, and we have not yet determined the microemulsion windows for systems made using these surfactants.

EXAMPLE 4

Preparation of Stable E/F Microemulsions Containing Film-Forming Polymers. After demonstrating that ethanol could be incorporated into E/F microemulsions in a sufficient amount, we then sought to incorporate ethyl cellulose dissolved in ethanol into the same microemulsion. Pharmaceutical grade ethyl cellulose with National Formulary (NF) designation was obtained from Hercules, Inc. (Wilmington, Del.). Six different molecular weights, all having 48.0–49.5% ethoxyl content, were obtained (ethyl cellulose N7, N10, N14, N22, N50, and N100). Our previous research in film-forming ethyl cellulose-based gels showed that films made with 1:1 blends of the higher molecular weight ethyl celluloses, N50 and N100, produced the strongest films. We deduced from this that the same blend would produce the most stable solid nanoparticles when exposed to biological fluids. Our intent was to identify an E/F microemulsion that could incorporate as high of a weight percentage of N50 and N100 as possible. Fortunately, the higher molecular weight ethyl cellulose polymers also precipitate more rapidly than the lower molecular weight polymers when ethanolic solutions of these polymers are exposed to water. More rapid precipitation of ethyl cellulose in the E/F microemulsions may be needed to entrap a greater amount of plasmid DNA. For these experiments, we added ethanol containing various types and concentrations of dissolved ethyl cellulose to perflubron/surfactant (70:30 w/w) mixtures. The mixtures were visually observed for the existence of the expected microemulsion window and/or whether ethyl cellulose remained dissolved in the E/F microemulsion. For all E/F microemulsions, the incorporation of ethyl cellulose had no effect on the formation of the E/F microemulsions or the width of the microemulsion window. As shown in Table 3, the incorporation of ethyl cellulose into the E/F microemulsion was maximized using the PDFOA surfactant. In an E/F microemulsion made with perflubron (0.508 g), PDFOA (0.214 g), and ethanol (0.228 g) with 5% ethyl cellulose, the stable microemulsion contained 11.4 mg of dissolved ethyl cellulose (N50/N100 1:1 w/w).

TABLE 3

Incorporation of Ethyl Cellulose Film-Forming Polymers into the Ethanol Dispersed Phase of E/F Microemulsions

| Fluoro surfactant | Ethyl Cellulose (Type) | Maximum Conc. Of Ethyl Cellulose In Ethanol in E/F Microemulsions |
|---|---|---|
| FSN-100 | N50/N100(1:1) | < 0.25% |
| FSN-100 | N50 | 0.25% |
| FSN-100 | N22, orN14 | 0.50% |
| FSN-100 | N10 | 1.0% |
| FSO-100 | N50/N100 (1:1) or N50 | < 0.25% |
| PDFOA | N50/N100(1:1) | 5% |

EXAMPLE 5

Modeling of E/F microemulsions: An ethanol-in-fluorocarbon(E/F) microemulsion was made having the following components: perflubron (0.7382 g), PDFOA (0.3195 g), and ethanol (0.3603 g). The weight of ethanol corresponded to 25.4% w/w of the final microemulsionor 65.7% of the microemulsion window (see FIG. 2). The average droplet size of 34.9 nm determined by photon correlation spectroscopy (dynamic light scattering at 11.3° for 300 seconds) agreed very well with the predicted ethanol droplet size based on simple mathematical modeling of surfactant-coated ethanol droplets. The total surface area of ethanol droplets that have an average diameter of 34.9 nm can be calculated in a series of equations as follows:

Volume of one ethanol droplet=$\pi d^3/6 = 2.226 \times 10^{-17}$ cm$^3$ (Equation 1)

Total number of ethanol droplets=(0.3603 g*0.814 g/cm$^3$)/$2.258 \times 10^{-17}$ cm$^3$=$1.989 \times 10^{16}$ droplets (Equation 2)

Total surface area of each droplet=$\pi d^2 = 3.827 \times 10^{-11}$ cm$^2$ (Equation 3)

Total surface area of all ethanol droplets=$1.989 \times 10^{16}$ droplets*$3.827 \times 10^{-11}$ cm$^2$=760966 cm$^2$. (Equation 4)

If we assume that PDFOA head-group (Mw 414.06 g/mol) occupies a space of 30 Å$^2$, then we can calculate the number of PDFOA molecules needed to cover the total surface area of all ethanol droplets from Equation 4 as:

Total number of PDFOA molecules needed to cover the total surface area of all ethanol droplets=760966 cm$^2$/$30 \times 10^{-16}$ cm$^2$=$2.537 \times 10^{20}$ molecules of PDFOA. (Equation 5)

Thus, $2.537 \times 10^{20}$ molecules of PDFOA would theoretically be needed to coat all of the surface area provided by all of the ethanol droplets. The ratio of ethanol to PDFOA molecules 65.7% through the microemulsion window was 10:1. We showed that if we continued adding ethanol to this E/F microemulsion to reach 100% of the microemulsion window, a total of 833 μL (or 0.678 g) ethanol could be added until the microemulsion became turbid. Deriving the same equations as shown above, it can be demonstrated that theoretically 0.3282 g PDFOA is needed to form a microemulsion incorporating 0.678 g ethanol ($8.864 \times 10^{21}$ molecules) into droplets having an average droplet size of 34.9 nm. The actual amount of PDFOA used to prepare the microemulsion was 0.3195 g which was within 3% of the predicted amount (0.3195 g/0.3282 g=0.973 or 97.3%) based on the measured droplet size of ethanol. Thus, this simple modeling supports the formation of a E/F microemulsion as well as the particle sizing method used.

EXAMPLE 6

Figure 3:
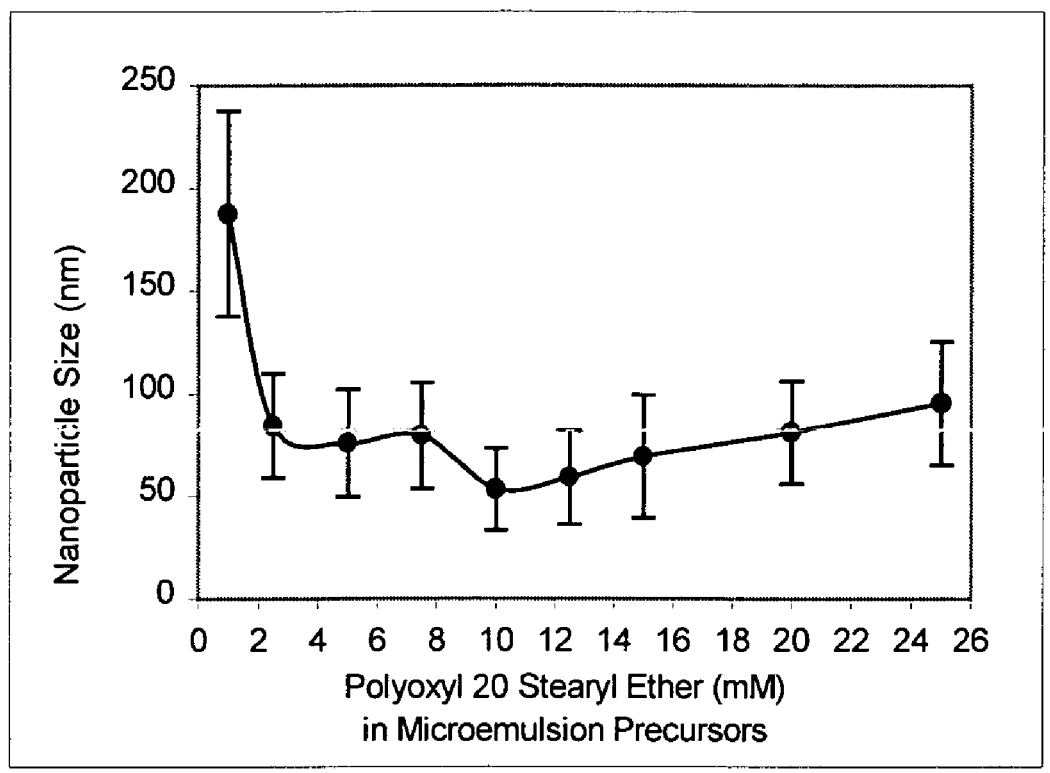
FIG. 3 Particle size of cured emulsifying wax nanoparticles (2 mg/mL) made from oil-in-water microemulsion precursors as a function of final surfactant (Brij 78, polyoxyl 20 stearyl ether) concentration in the microemulsion precursors.

To determine the existence of an oil-in-water microemulsion window for the microemulsion precursor, exactly two (2) milligrams of emulsifying wax were weighed accurately into ten separate 7-mL glass vials and melted at 50° C. on a temperature calibrated magnetic hot plate. Water (0.2 μm filtered) was then added (750–1000 μL) to form a homogeneous milky slurry in the stirring water at 50° C. To form the microemulsion precursor, the surfactant polyoxy 20 stearyl ether (100 mM) in water was added (0–250 μL) so that the final surfactant concentration ranged from 0 mM to 25 mM in the ten vials. The microemulsion precursor was then removed from heat (52–54° C.) and allowed to cool to 25° C. while stirring. When cooled, visual inspection showed that systems with final surfactant concentration less than 2.5 mM were precipitated, systems with final surfactant concentration between 2.5 mM and 10 mM were either very slightly turbid or clear, and systems with a final surfactant concentration greater than 10 mM were either very turbid or precipitated. Thus, an apparent microemulsion window was defined. One hundred (100) μL of each cooled system was taken and diluted with 900 μL water. The particle size of the diluted solid nanoparticles was determined using a Coulter N4 Plus Sub-Micron Particle Sizer at 20° C. by scattering light at 90° for 120 seconds. The particle sizes of the cured solid nanoparticles as a function of surfactant concentration are shown in FIG. 3. The particle sizes of systems with no surfactant added could not be determined since the systems contained precipitates that were greater than 3000 nm in diameter. In general, the particle size results agreed with the visual observations and suggested the following; 1) solid nanoparticles less than 100 nm could be engineered from the liquid matrix oil-in-water microemulsion precursor, and 2) the resulting clarity and particle size were related to the final concentration of the surfactant used. The droplet size of the oil phase in the microemulsion nanotemplates made with a final surfactant concentration of 10 mM was measured at 55° C. and was found to be 11±3 nm demonstrating that oil-in-water microemulsion precursor could be made. To determine if the measured droplet sizes in either the microemulsion nanotemplate or the cured solid nanoparticles were due to the presence of surfactant micelles, samples were made as described above with no emulsifying wax and with final surfactant concentrations ranging from 0 mM to 100 mM in water. Interestingly, no published critical micellar concentration (CMC) value could be found for polyoxyethylene 20 stearyl ether. It is likely that the relatively heterogeneous nature of the polymeric surfactant makes the determination of its CMC difficult using conventional techniques. Photon correlation spectroscopy, using a Coulter N4 Plus Submicron Particle Sizer, was used to determine the existence and the size of the surfactant micelles. The results indicated that the surfactant does begin to form micelles (5–20 mm) between a concentration of 0.5 mM to 1 mM in water. However, these micelles are clearly absent in the cured solid nanoparticles indicating that the 50–100 nm nanoparticles could be engineered directly from the microemulsion precursors.

EXAMPLE 7

Figure 4:
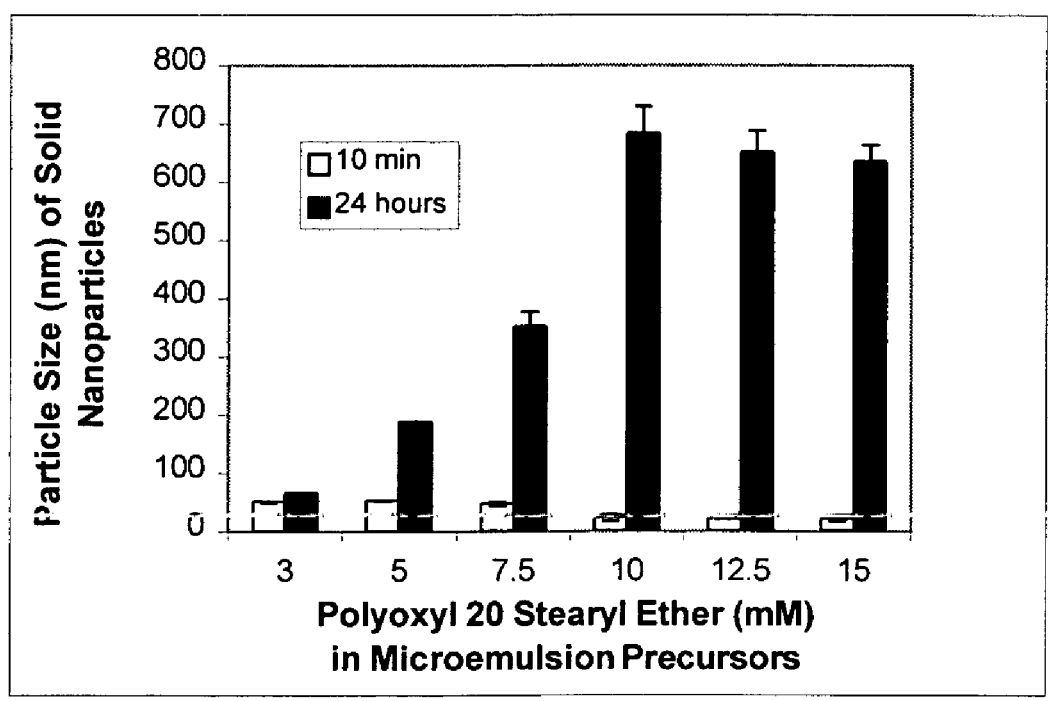
FIG. 4 Stability of cured emulsifying wax nanoparticles (2 mg/mL) as a function of final surfactant (Brij 78, polyoxyl 20 stearyl ether) concentration in the microemulsion precursors.

Stability of cured emulsifying wax nanoparticles over time: Emulsifying wax nanoparticles (2 mg/mL) were prepared as described in Example 6 using final concentrations of Brij 78 surfactant between 3 mM and 15 mM. The particle size of cured nanoparticles was determined both at 10 minutes and 24 hours after curing. For particle size analysis, one hundred microliters (100 µL) of each preparation was taken and diluted with 900 µL distilled water. As shown in FIG. 4, although cured nanoparticles made with higher concentrations of Brij 78 surfactant were initially smaller than those made with lower concentrations of Brij 78, the nanoparticle made with higher concentrations of Brij 78 agglomerated to larger particles over 24 hours. Ideally, a final surfactant concentration of 3 mM produced stable nanoparticles. These findings were unexpected and the reason for this phenomena is still unknown. It is clear, however, that a non-obvious and optimal amount of surfactant is needed to both engineer stable microemulsion precursors as well as stable cured nanoparticles from these precursors.

EXAMPLE 8

Figure 5:
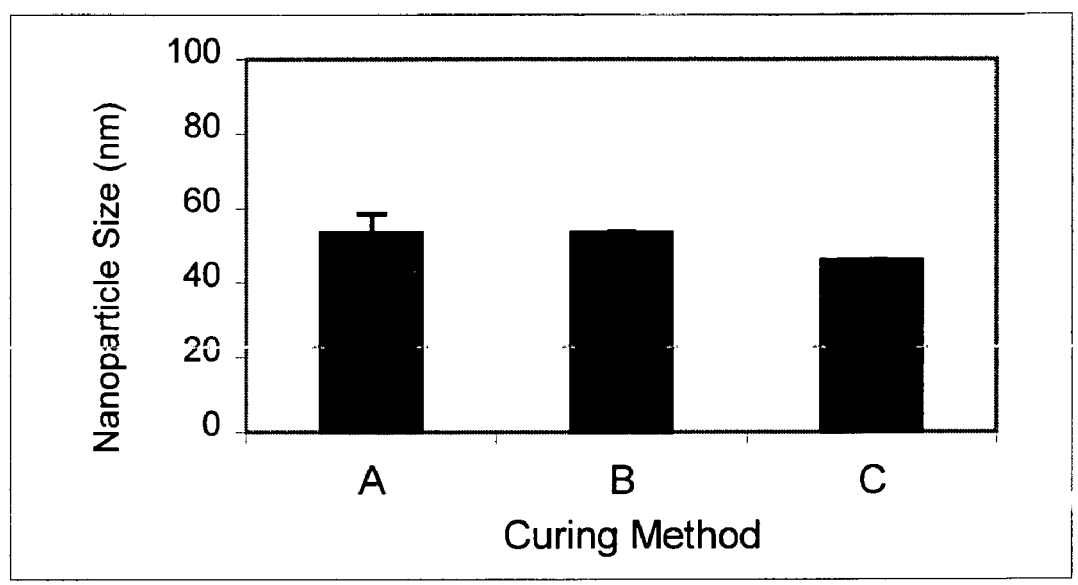
FIG. 5 The effect of three different curing methods of oil-in-water microemulsion precursors on the resulting particle size of Brij 72 nanoparticles made with Tween 80 as the surfactant. Method A) cooling of the undiluted oil-in-water microemulsion at 55° C. to room temperature while stirring, Method B) cooling of the oil-in-water microemulsion at 55° C. by placing undiluted in a refrigerator at 4° C., and Method C) diluting (1/10) the oil-in-water microemulsion at 55° C. with water at 4° C.

Preparation of Brij 72 nanoparticles. Three separate samples of Brij 72 nanoparticles were engineered using the following process. Brij 72 (2 mg) was melted at 50–55° C. and dispersed in 970 microliters of water at the same temperature. Thirty microliters of solution of Tween 80 (10% v/v in water) was added to produce a clear oil-in-water microemulsion at approximately 55° C. The oil droplet size of liquid Brij 72 was measured by photon correlation spectroscopy to be 22.2±1.8 nanometers at approximately 55° C. Brij 72 nanoparticles were cured by three different methods as follows: Method A) cooling of the undiluted oil-in-water microemulsion at 55° C. to room temperature while stirring, Method B) cooling of the oil-in-water microemulsion at 55° C. by placing undiluted in a refrigerator at 4° C., and Method C) diluting (1/10) the oil-in-water microemulsion at 55° C. with water at 4° C. The results as shown in FIG. 5 demonstrate that the method of curing had no effect on the size of nanoparticles formed. Further, Method A illustrated a key advantage of simply allowing the oil-in-water microemulsion to cool to room temperature to form useful solid nanoparticles. This method allows for rapid, reproducible, and cost-effective method to engineer useful nanoparticles.

EXAMPLE 9

Figure 6:
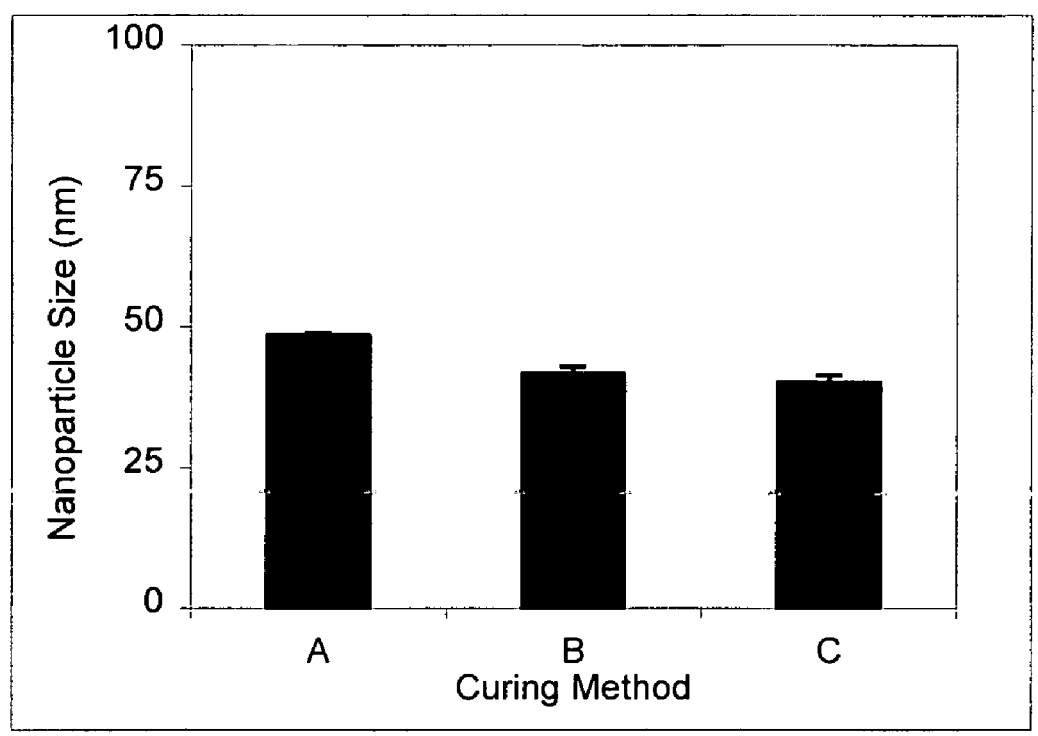
FIG. 6 The effect of three different curing methods of oil-in-water microemulsion precursors on the resulting particle size of emulsifying wax nanoparticles made with Brij 78 as the surfactant. Method A) cooling of the undiluted oil-in-water microemulsion at 55° C. to room temperature while stirring, Method B) cooling of the oil-in-water microemulsion at 55° C. by placing undiluted in a refrigerator at 4° C., and Method C) diluting (1/10) the oil-in-water microemulsion at 55° C. with water at 4° C.

Preparation of emulsifying wax nanoparticles. Three separate samples of emulsifying wax nanoparticles were engineered using the following process. Emulsifying wax (2 mg) was melted at 50–55° C. and dispersed in 970 microliters of water at the same temperature. Thirty microliters 100 mM Brij 78 were added to produce a clear oil-in-water microemulsion at approximately 55° C. The oil droplet size of liquid emulsifying wax was measured by photon correlation spectroscopy to be 24.5±0.4 nanometers at approximately 55° C. Emulsifying nanoparticles were cured by three different methods as follows: Method A) cooling of the undiluted oil-in-water microemulsion at 55° C. to room temperature while stirring, Method B) cooling of the oil-in-water microemulsion at 55° C. by placing undiluted in a refrigerator at 4° C., and Method C) diluting (1/10) the oil-in-water microemulsion at 55° C. with water at 4° C. The results as shown in FIG. 6 demonstrate that the method of curing had no effect on the size of nanoparticles formed. Further, Method A illustrated a key advantage of simply allowing the oil-in-water microemulsion to cool to room temperature to form useful solid nanoparticles. This method allows for rapid, reproducible, and cost-effective method to engineer useful nanoparticles.

Further, the solid nanoparticles made from Method A were subjected to ultracentrifugation at 50,000 rpm for 30 minutes. Photon correlation spectroscopy analysis showed that these ultracentrifugation conditions had no effect on the intensity of light scattering or particle size indicating a very stable colloidal suspension.

EXAMPLE 10

Figure 7:
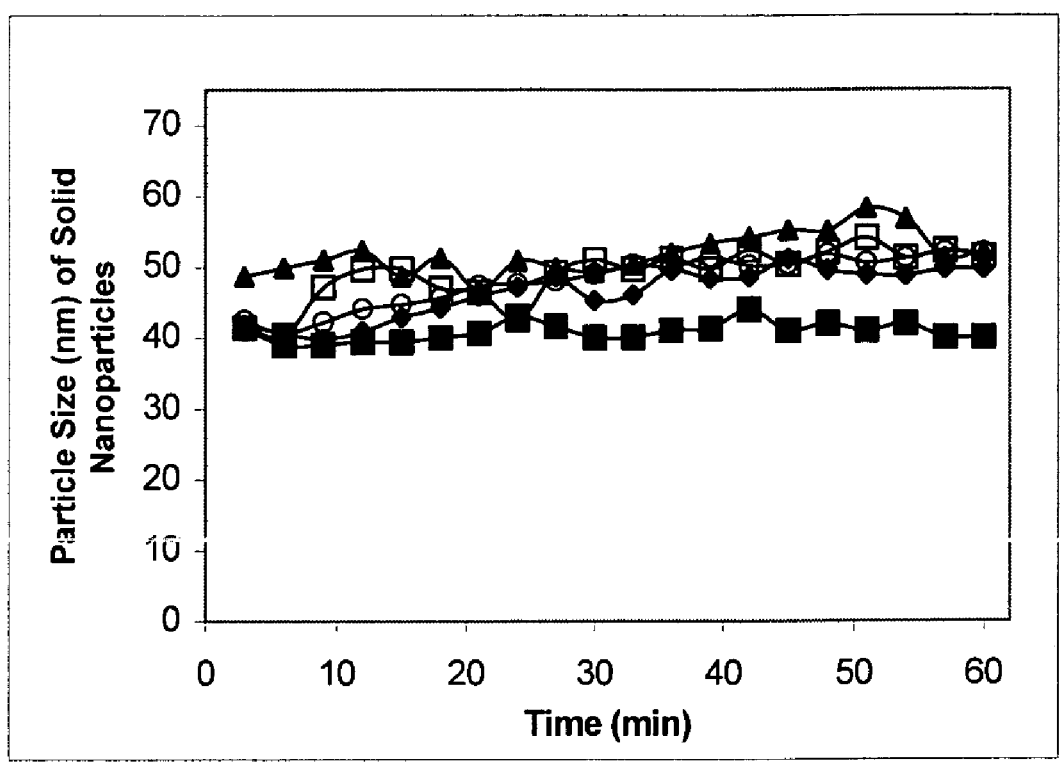
FIG. 7 The stability of Brij 72 nanoparticles challenged with different media at 37° C.: (♦) water, (■) 10% FBS ( ) 10 mM PBS, (O) 150 mM NaCl, ( ) 10% lactose.

Stability of nanoparticles in biological conditions: To assess the potential stability of nanoparticles in biological media, Brij 72 nanoparticles (2 mg/mL) were diluted 1:10 with 10% fetal bovine serum (FBS), 10 mM phosphate buffered saline (pH 7.4), 10% lactose, or 150 mM NaCl. The particle size of nanoparticles in each media was monitored for 60 minutes at 37° C. As shown in FIG. 7, cured Brij 72 nanoparticles challenged with various biological media at 37° C. were found to be stable over 60 minutes under all conditions.

EXAMPLE 11

Figure 8:
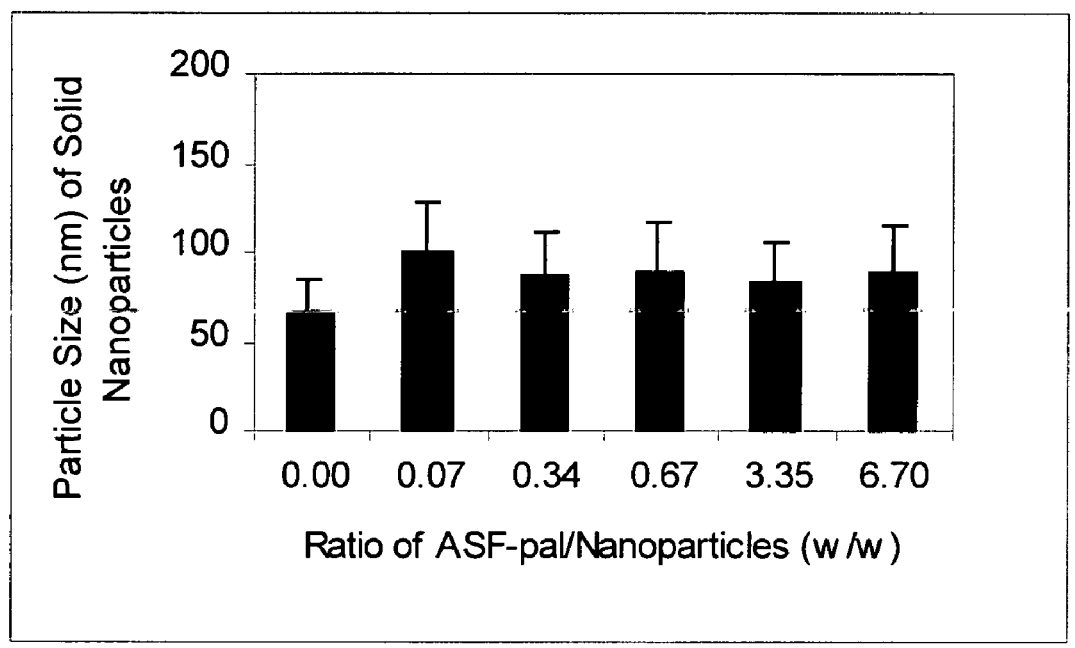
FIG. 8 Particle size of cured emulsifying wax nanoparticles coated with different amounts of a hepatocyte-specific ligand, asialofetuin-palmitate (AS F-pal).

Incorporation of cell-specific ligand on nanoparticles: To determine the feasibility of adding a hydrophobized cell-specific targeting ligand to the cured solid nanoparticles, asialofetuin-palmitate (ASF-pal) was synthesized and purified. Asialofetuin was derivatized with about 12 palmitate 'arms' per molecule as measured by a colorimetric hydroxamic acid reaction assay. ASF-pal (1–100 µL; 13.4 µg/mL water) was added to cured solid nanoparticles in water so that the final concentration of nanoparticles was 200 µg nanoparticles per 1 mL. Stirring was continued at 25° C. for a total of 1 hour to ensure complete adsorption/insertion of the palmitate arm of ASF-pal into the nanoparticles. The results as shown in FIG. 8 demonstrate that even very high concentrations of ASF-pal could be added to the nanoparticles with only a small effect on the particle size. As controls, the particle size of ASF-pal alone in water at a concentration of either 67 µg/mL or 1340 µg/mL were measured. The results showed that ASF-pal formed micelles (3–15 nm) at 67 µg/mL At a concentration of 1340 µg/mL, ASF-pal formed a mixture of micelles (3–10 nm) as well as larger aggregates (40–300 nm). It was apparent from these results that a hydrophobized cell-specific targeting ligand could be added to cured nanoparticles.

EXAMPLE 12

Figure 9:
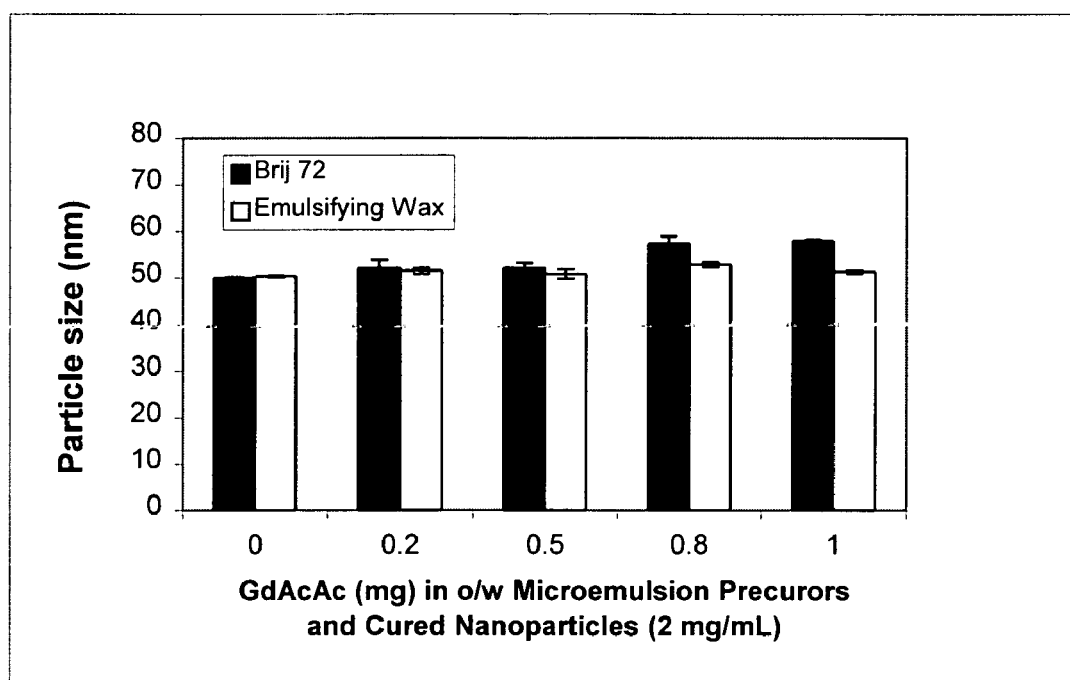
FIG. 9 Entrapment of Gadolinium Acetylactetonate (GdAcAc) in both emulsifying wax and Brij 72 nanoparticles.
Figure 10:
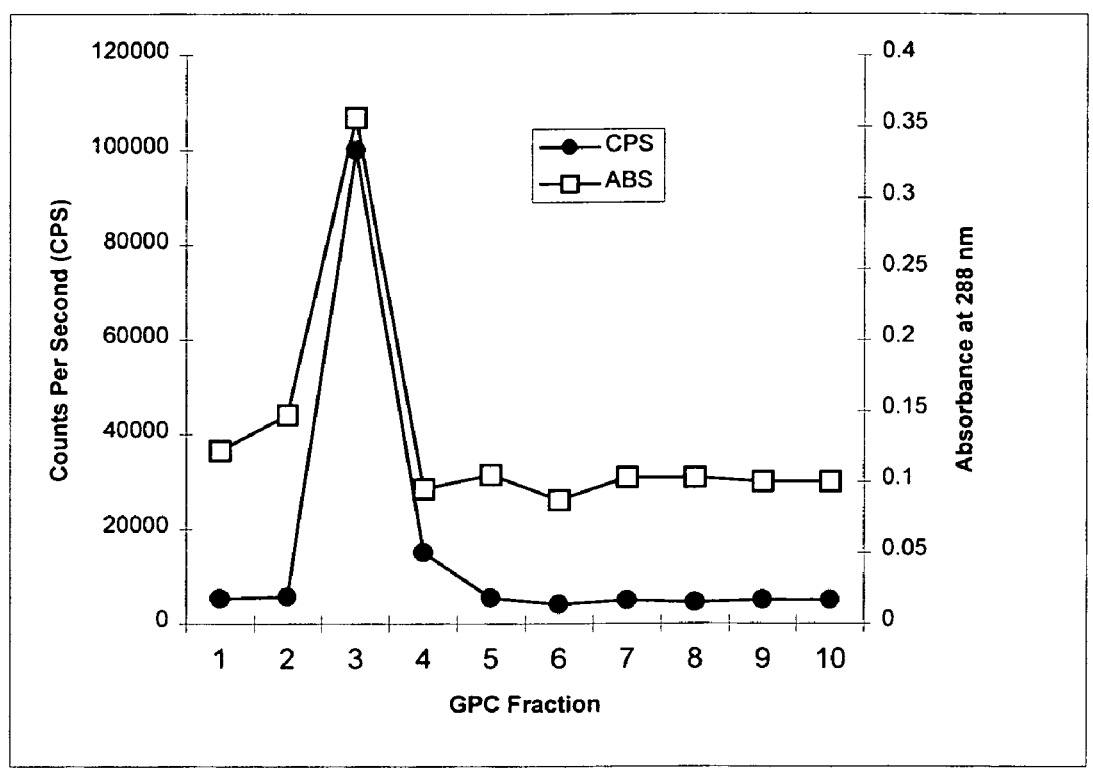
FIG. 10 Entrapment efficiency of Gadolinium Acetylactetonate (GdAcAc) in emulsifying wax nanoparticles as determined by gel permeation chromatography (GPC) elution profiles. Nanoparticles were detected by laser light scattering (counts per second, CPS) and entrapped GdAcAc was detected by absorbance at 288 nm.

It was discovered that the solubility of Gadolinium acetylacetonate (GdAcAc), a potential agent for neutron capture therapy of tumors, in water could effectively be increased by at least 4000-fold using the methods described in this invention. Specifically, the solubility of GdAcAc is only 1 mg per 2000 mL water However, utilizing the said methods described in this invention to entrap GdAcAc in stable nanoparticles having diameters of about 50 nanometers, only 1 milliliter of water is required to solubilize 2 mg GdAcAc. Various amounts (0.1 mg to 1 mg) of gadolinium acetylacetonate were entrapped in both emulsifying wax and Brij 72 nanoparticles (2 mg/mL). As shown in FIG. 9, the entrapment of GdAcAc had little or no effect on the resulting particle sizes of the cured nanoparticles. Entrapment efficiencies of GdAcAc in nanoparticles were determined using gel permeation chromatography (Sephadex G75; 30 cm×0.5 cm column) with water as the mobile phase. One hundred microliters (100 μL) of nanoparticles (2 mg/mL) containing GdAcAc (0.5 mg/mL) was eluted down the column. Each fraction (1 ml) was monitored using light both scattering (counts per second) and UV absorption of GdAcAc (at 288 nm). As shown in FIG. 10, GPC analysis confirmed that GdAcAc co-eluted with nanoparticles and that the apparent entrapment efficiency of GdAcAc in nanoparticles was approximately 100%.

EXAMPLE 13

Figure 11:
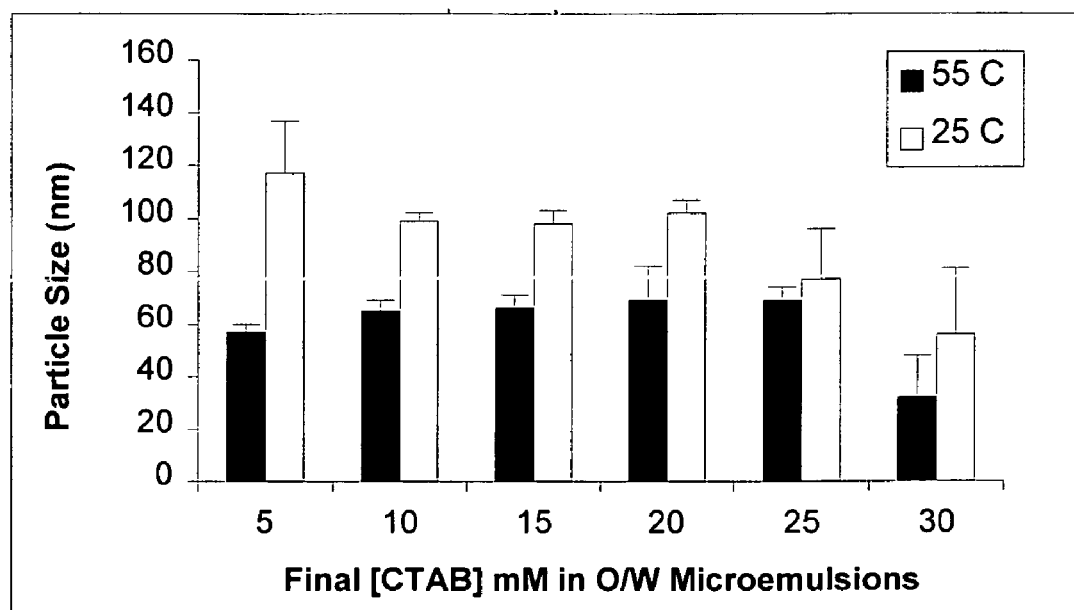
FIG. 11 Particle size analysis of warm o/w microemulsion precursors at 55° C. and cured (cooled) emulsifying wax nanoparticles at 25° C. The cationic nanoparticles were made using hexadecyltrimethylammonium bromide (CTAB) as the surfactant.

Preparation of cationic nanoparticles made from microemulsion precursors: Exactly 2 mg of emulsifying wax was placed into six 7-ml glass scintillation vials. After melting at 50–55° C., water was added to form a homogenous milky slurry. Different volumes of a hexadecyltrimethylammonium bromide (CTAB) stock solution (50 mM in water) was added while stirring to obtain a final CTAB concentration of 5 to 30 mM. After 3–5 min, the milky slurry turned clear or stayed cloudy, depending on the amount of CTAB used. The droplet size of the microemulsion was measured at 55° C. using a Coulter N4 Plus Submicron Particle Sizer (Coulter Corporation, Miami, Fla.) at a 90° angle for 90 seconds. These microemulsions were then cooled down (cured) to room temperature while stirring to form nanoparticles. The nanoparticle suspension was diluted 10 times with water (0.22 mm filtered) and the particle size was measured as above. When the required volume of CTAB (50 mM) solution was added into the milky slurry wax in warm suspension, the suspension turned clear within seconds if the final CTAB concentration was greater than 10 mM. For the samples with final CTAB concentration of 5 mM or below, the samples turned slightly turbid. As shown in FIG. 11, the droplet sizes of the warm microemulsions (at 55° C.) were in the range of 30–70 nm and cured nanoparticles (at 25° C.) were in the range of 60–120 nm.

EXAMPLE 14

Figure 12:
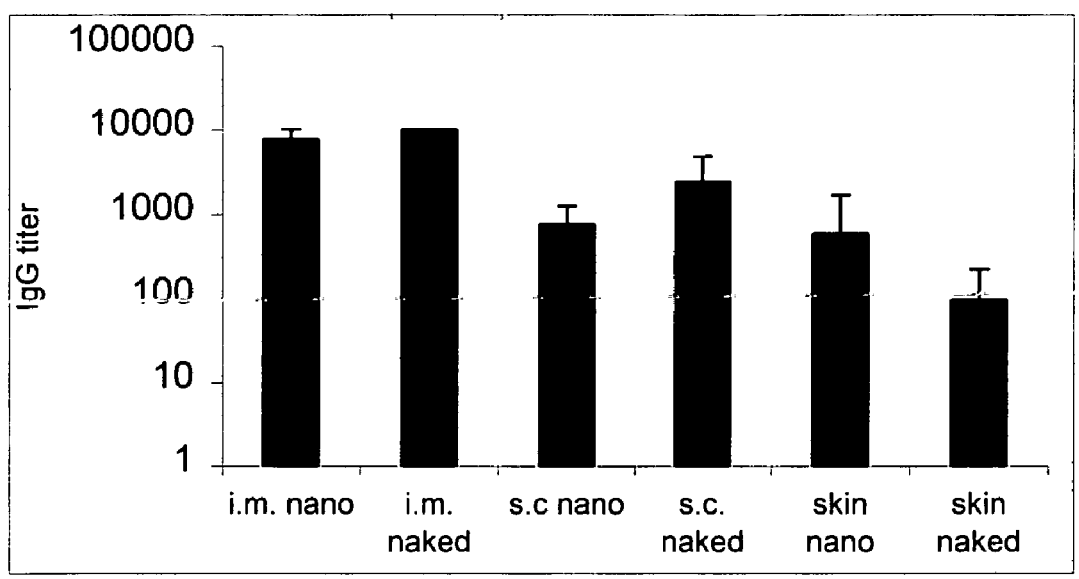
FIG. 12 Antigen-specific IgG levels in sera to expressed β-galactosidase 28 days after the administration of pDNA-coated nanoparticles ("nano") and 'naked' pDNA to Balb/C mice by three routes (intramuscular, "i.m."; subcutaneous, "s.c."., and topically to skin, "skin"). See Example 14 for more details. Mice (n=5/group) were immunized with 40 µg pDNA on day 0, 7, and 14. IgG titers are the mean±standard deviation of all mice.

Preparation of cationic nanoparticles with adsorbed plasmid DNA for genetic immunization: Cationic nanoparticles comprised of 6 mg emulsifying wax per 1 mL water containing a final concentration of 15 mM CTAB were prepared as described in Example 13. Free CTAB was separated from the cured nanoparticles using a Sephadex G-75 column (14×230 mm) and using 10% lactose as the mobile phase. Two milliliters of the cured nanoparticle suspension was applied to the column. The particle size and zeta potential of the purified cationic nanoparticles was measured and found to be 99±27 nm and 35.8±2.3 mV, respectively. Plasmid DNA (CMV-β-galactosidase) was coated on the surface of the nanoparticle by gently mixing the required amount of pDNA and nanoparticle suspension to obtain a final pDNA concentration of 400 μg/mL. After the addition of pDNA to the cationic nanoparticles, the particle size and zeta potential of the pDNA-coated nanoparticles was 245±25 nm and −47.7±1.2 mV, respectively. The change in particle size and zeta-potential demonstrated that pDNA was successfully coated on the cationic nanoparticles. pDNA-coated nanoparticles and 'naked' DNA were administered to Balb/C mice (10–12 weeks old) by three different routes (intramuscular injection, i.m.; subcutaneous injection, s.c., or by topical application to skin) on day 0, 7, and 14. The pDNA dose on each day was 40 μg. On day 28, the IgG titers in sera were determined and are plotted in FIG. 12. Sera IgG titers at day 28 resulting from immunization by pDNA-coated nanoparticles and 'naked' DNA after intramuscular and subcutaneous administration were comparable. However, a surprising finding was observed after topical administration of formulations to skin. Mice immunized with pDNA-coated nanoparticles had an approximately 10-fold increase in IgG titers over mice immunized with 'naked' pDNA.

EXAMPLE 15

Figure 13:
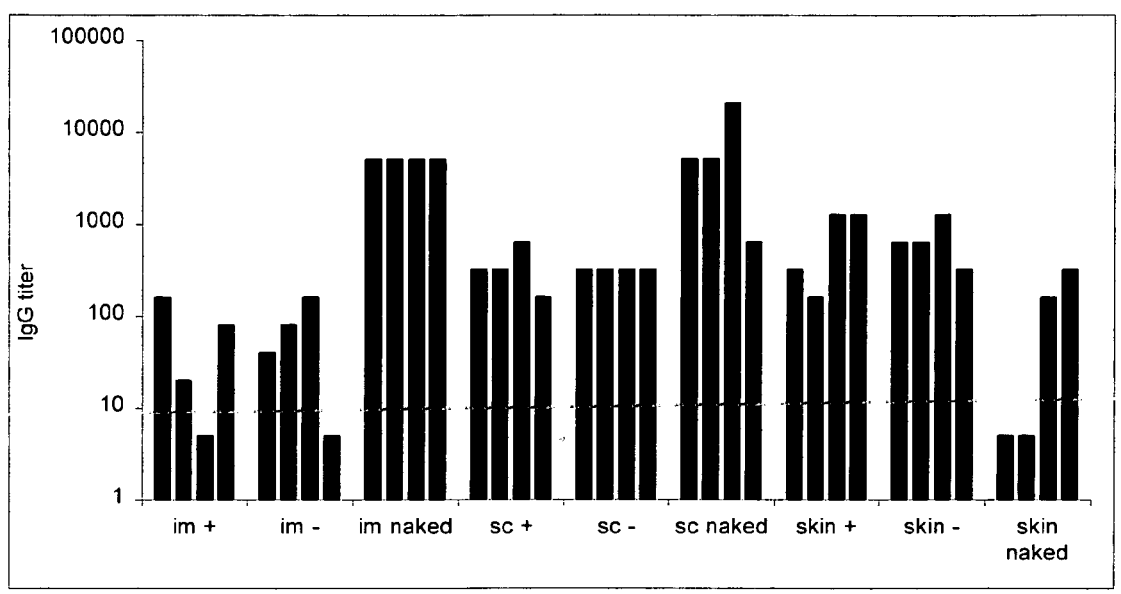
FIG. 13 Antigen-specific IgG levels in sera to expressed β-galactosidase 28 days after the administration of either net positively-charged pDNA-coated nanoparticles ("+"), net negatively-charged pDNA-coated nanoparticles ("–"), or 'naked' pDNA to Balb/C mice by three routes (intramuscular, "i.m."; subcutaneous, "s.c.", and topically to skin, "skin"). See Example 15 for more details. Mice (n=4/group) were immunized with 4 µg pDNA on day 0, 7, and 14. Results are expressed as the individual titer for each mouse.
Figure 14:
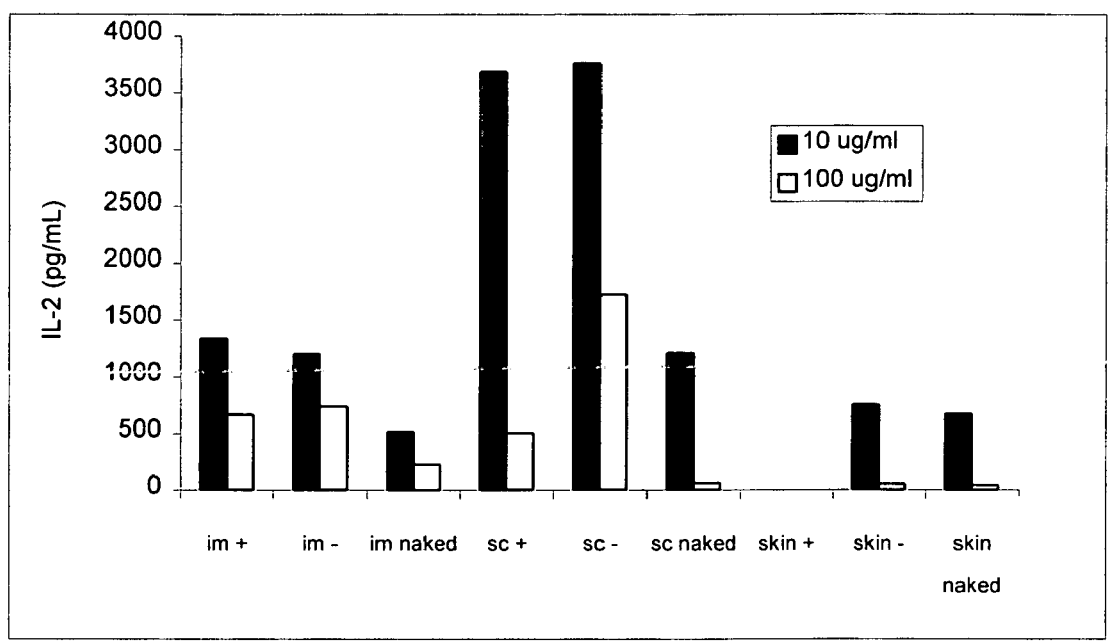
FIG. 14 Secretion of Interleukin-2 (IL-2) from isolated splenocytes (1×10$^6$ cells) from immunized Balb/C mice after in-vitro exposure to β-galactosidase protein for 60 hours at a concentration of either 10 µg/mL or 100 µg/mL. Mice were immunized with either net positively-charged pDNA-coated nanoparticles ("+"), net negatively-charged pDNA-coated nanoparticles ("–"), or 'naked' DNA to Balb/C by three routes (intramuscular, "i.m."; subcutaneous, "s.c."., and topically to skin, "skin"). See Example 15 for more details. Mice were immunized with 4 µg pDNA on day 0, 7, and 14. Results are expressed as the mean IL-2 levels from pooled splenocytes harvested on day 28.
Figure 15:
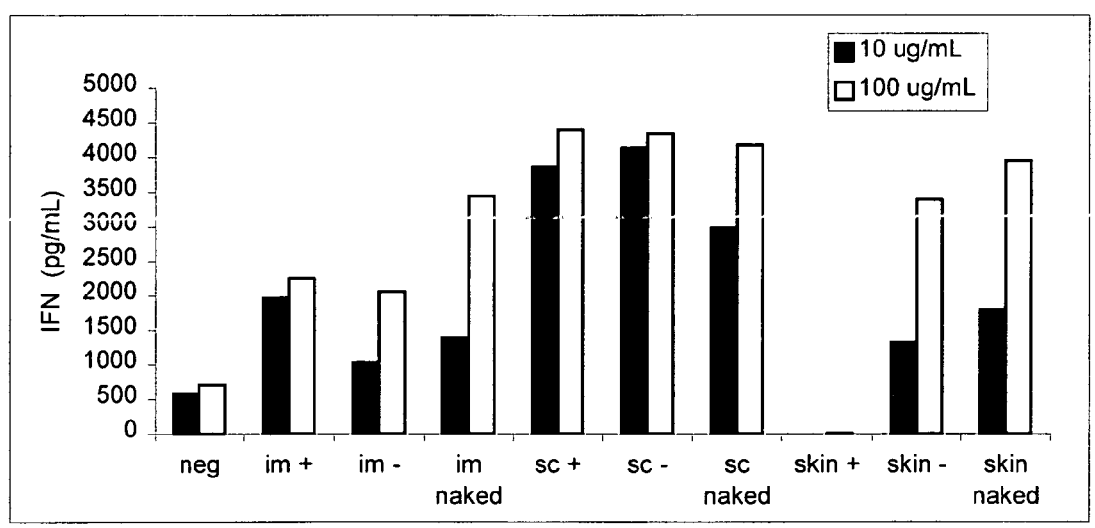
FIG. 15 Secretion of Interferon-γ (INF-γ) from isolated splenocytes (1×10$^6$ cells) from immunized Balb/C mice after in-vitro exposure to β-galactosidase protein for 60 hours at a concentration of either 10 µg/mL or 100 µg/mL. Mice were immunized with either net positively-charged pDNA-coated nanoparticles ("+"), net negatively-charged pDNA-coated nanoparticles ("–"), or 'naked' DNA to Balb/C by three routes (intramuscular, "i.m."; subcutaneous, "s.c."., and topically to skin, "skin"). See Example 15 for more details. Mice were immunized with 4 µg pDNA on day 0, 7, and 14. Results are expressed as the mean INF-γ levels from pooled splenocytes harvested on day 28.
Figure 16:
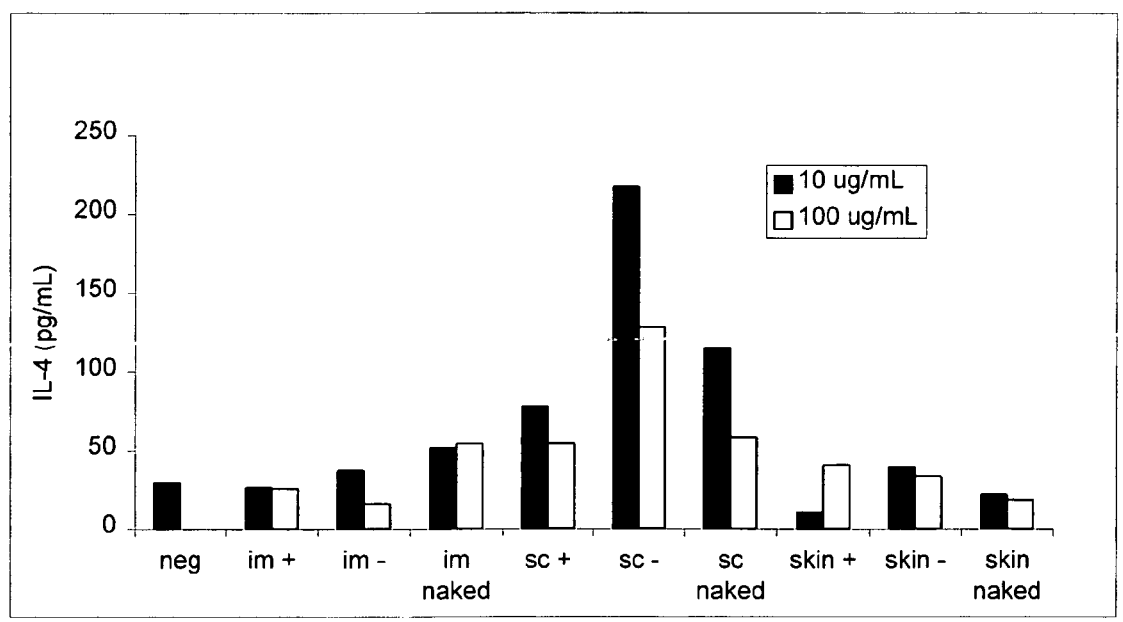
FIG. 16 Secretion of Interleukin-4 (IL-4) from isolated splenocytes (1×10$^6$ cells) from immunized Balb/C mice after in-vitro exposure to β-galactosidase protein for 60 hours at a concentration of either 10 µg/mL or 100 µg/mL. Mice were immunized with either net positively-charged pDNA-coated nanoparticles ("+"), net negatively-charged pDNA-coated nanoparticles ("–"), or 'naked' DNA to Balb/C by three routes (intramuscular, "i.m."; subcutaneous, "s.c."., and topically to skin, "skin"). See Example 15 for more details. Mice were immunized with 4 µg pDNA on day 0, 7, and 14. Results are expressed as the mean IL-4 levels from pooled splenocytes harvested on day 28.

Cationic emulsifying wax nanoparticles containing two different concentrations of CTAB were prepared as described in Example 13 above. Plasmid DNA (CMV-β-galactosidase) was coated on the surface of the nanoparticle by gentle mixing to form, 1) a pDNA-coated nanoparticle having a net positive charge with pDNA at a final concentration of 40 μg/mL, and 2) a pDNA-coated nanoparticle having a net negative charge with pDNA at a final concentration of 40 μg/mL. pDNA-coated nanoparticles (negatively-charged and positively-charged) and 'naked' DNA were administered to Balb/C mice (10–12 weeks old) by three different routes (intramuscular injection, i.m.; subcutaneous injection, s.c., or by topical application to skin) on day 0, 7, and 14. The pDNA dose on each day was 4 μg. The IgG titers in sera were determined and are plotted in FIG. 13. The results were similar to those obtained and reported in Example 14 above. Sera IgG titers at day 28 resulting from immunization by pDNA-coated nanoparticle were lower than 'naked' pDNA for the 4 μg doses after both intramuscular and subcutaneous administration. However, mice immunized with pDNA-coated nanoparticles by topical application to skin showed up to 1–2 log increases in IgG titers as compared to mice immunized with 'naked' pDNA. As shown in FIG. 14, mice immunized with pDNA-coated nanoparticles induced greater IL-2 production from stimulated splenocytes by all three routes of administration. For example, IL-2 production from stimulated splenocytes was approximately 3-fold higher after immunization with pDNA-coated nanoparticles by both intramuscular and subcutaneous injection as compared to 'naked' pDNA. As shown in FIG. 15, IFN-γ production from stimulated splenocytes was comparable after immunization with pDNA-coated nanoparticles and 'naked' pDNA by all three routes. As shown in FIG. 16, IL-4 production from stimulated splenocytes was comparable after immunization with pDNA-coated nanoparticles and 'naked' pDNA by all three routes, except for subcutaneous administration of pDNA-coated nanoparticles that were net negatively-charged. Immunization with these pDNA-coated nanoparticles resulted in an approximately 2.4-fold increase in IL-4 production from stimulated splenocytes over 'naked' pDNA given by the same route.

EXAMPLE 16

Figure 17:
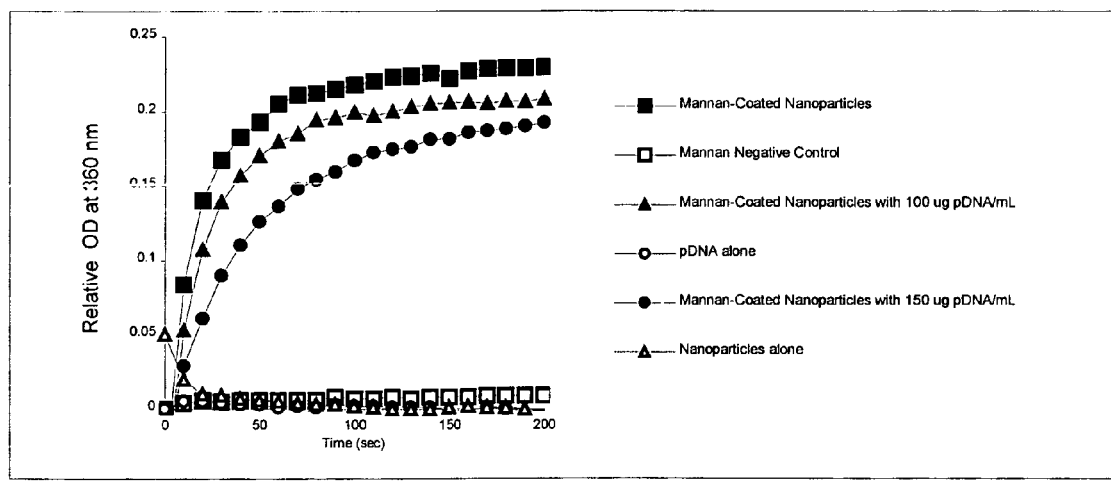
FIG. 17 Verification of Ligand-Coated Nanoparticles. Nanoparticles were coated with cholesterol-mannan as described in Example 16. Mannan-coated nanoparticles were purified by GPC to remove unincorporated or free chol-mannan. Various samples were added to Concanavalin A (Con-A; 1 mg/mL) and the increase in turbidity at 360 nm was measured for 200 seconds. A "mannan negative control" was taken from the same fraction that nanoparticles normally elute from the GPC column (fraction 2–4). This confirmed that the positive agglutination results from mannan-coated emulsifying wax nanoparticles were not caused by co-elution of nanoparticles with unincorporated chol-mannan.

Confirmation of cell-specific ligand on the surface of cured emulsifying wax nanoparticles: Cholesterol-mannan (Chol-mannan) was purchased from Dojindo (Gaithersburg, Md.). Various amounts of Chol-mannan were incorporated into cured nanoparticles either during the preparation of the o/w microemulsion precursor or by adsorbing it on the surface of cured nanoparticles as described in Example 11. Mannan-coated nanoparticles were purified by GPC to remove unincorporated or free chol-mannan. An in-vitro agglutination was be used to verify that mannan was on the surface of GPC purified nanoparticles. Con-A is tetrameric protein with four binding sites specific for terminal glucosyl or mannosyl residues. Binding to the mannan will cause agglutination (or aggregation) of the complex in solution resulting in an increase in turbidity. This assay was performed at room temperature by adding various samples to Con-A (1 mg/mL) in phosphate buffered saline, pH 7.4 with 5 mM calcium chloride and 5 mM magnesium chloride and monitoring the increase in turbidity at 360 nm for 200 seconds. As shown in FIG. 17, as expected, nanoparticles alone (uncoated) or pDNA alone resulted in no detectable agglutination of Con-A over 200 seconds. In comparison, mannan-coated nanoparticles and mannan-coated nanoparticles containing pDNA (at a concentration of 100 µg/mL or 150 µg/mL) caused significant agglutination of Con-A over 200 seconds as confirmed by the increase in absorbance. It was also shown that a "mannan negative control" also produced no agglutination of Con-A. This negative control was taken from the same fraction that nanoparticles normally elute from the GPC column (fraction 2–4). This confirmed that the positive agglutination results were not caused by co-elution of nanoparticles with unincorporated chol-mannan.

EXAMPLE 17

Figure 18:
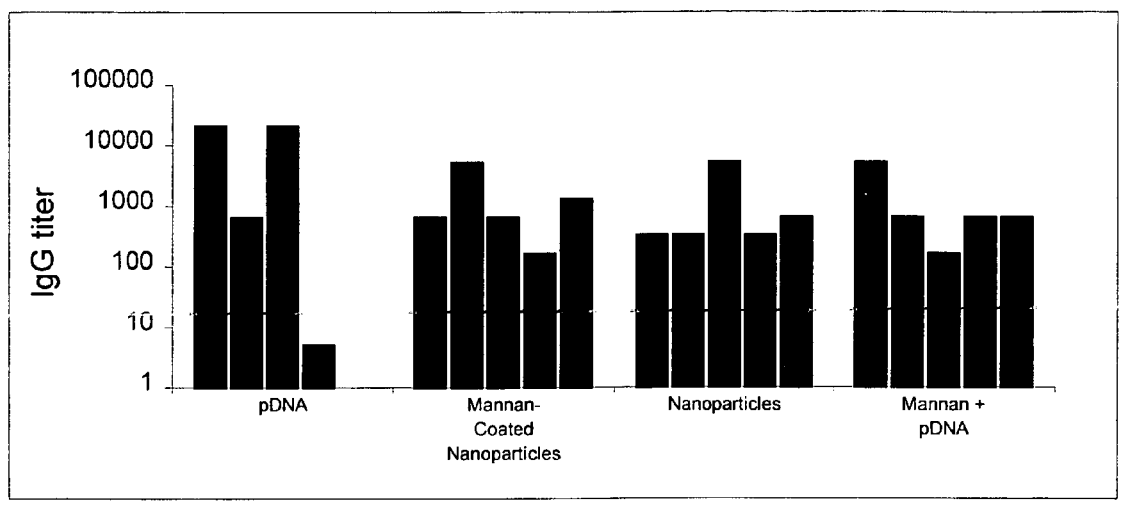
FIG. 18 Antigen-specific IgG levels in sera to expressed β-galactosidase 28 days after subcutaneous administration of 'naked' pDNA, mannan-coated nanoparticles with pDNA, nanoparticles with pDNA, or mannan with free pDNA. Mice were immunized with 10 µg pDNA on day 0, 7, and 14. See Example 17 for more details. Mice were immunized with 4 µg pDNA on day 0, 7, and 14. Results are expressed as the individual titer for each mouse. All groups had 5 mice except for pDNA which had 4 mice.
Figure 19:
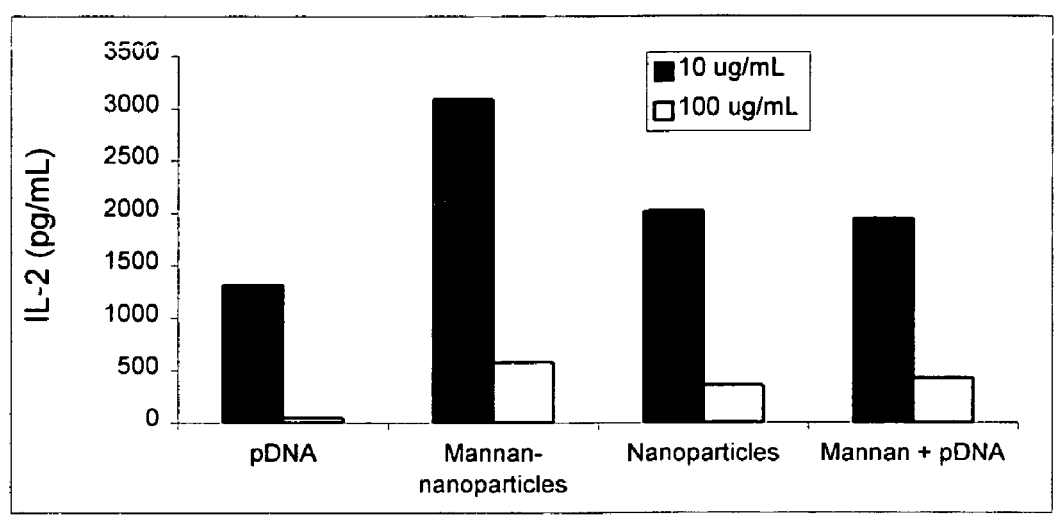
FIG. 19 Secretion of Interleukin-2 (IL-2) from isolated splenocytes (1×10$^6$ cells) from immunized Balb/C mice after in-vitro exposure to β-galactosidase protein for 60 hours at a concentration of either 10 µg/mL or 100 µg/mL.

Emulsifying wax nanoparticles made with CTAB as the surfactant were prepared. Chol-mannan and/or pDNA (CMV-β-galactosidase) were coated on the surface of the nanoparticles as described in Example 16 to prepare the following formulations, 1) pDNA alone, 2) mannan-coated nanoparticles with pDNA, 3) pDNA-coated nanoparticles, and 4) mannan plus free pDNA as a control. These formulations were administered to Balb/C mice (10–12 weeks old) by subcutaneous injection on day 0, 7, and 14. The pDNA dose on each day was 10 µg. The IgG titers in sera were determined on day 28 and are plotted in FIG. 18. Results are expressed as the individual titer for each mouse. All groups had 5 mice except for pDNA which had 4 mice. As shown in FIG. 18, the mean sera IgG titers at day 28 for all formulations were comparable. Two mice immunized with 'naked' pDNA had IgG titers that were clearly higher than any other mice, however, one mouse immunized with 'naked' pDNA could be considered a non-responder. As shown in FIG. 19, mice immunized with pDNA-coated nanoparticles or mannan-coated nanoparticles showed up to 2-fold greater IL-2 production from stimulated splenocytes as compared to 'naked' pDNA. As shown in FIG. 20, IFN-γ production from stimulated splenocytes (100 µg β-gal/mL) was comparable after immunization with pDNA-coated nanoparticles or mannan-coated nanoparticles and 'naked' pDNA. However, IFN-γ production from stimulated splenocytes (10 µg β-gal/mL) was up to 4-fold greater with pDNA-coated nanoparticles or mannan-coated nanoparticles as compared to 'naked' pDNA. Finally, as shown in FIG. 21, IL-4 production from stimulated splenocytes was significantly higher for all groups as compared to 'naked' pDNA which showed IL-4 levels near or at background.

EXAMPLE 18

Entrapment of plasmid DNA into nanoparticles engineered from microemulsion precursors: A significant challenge to the use of the new O/W microemulsion precursors is that plasmid DNA, a highly negatively-chargedhydrophilic molecule, would have to be contained in the oil phase if it were to be entrapped in the solid nanoparticles. To this end, a series of positively charged surfactants or lipids were screened as potential agents to complex and 'hydrophobize' plasmid DNA as described previously (Hara et al., 1997; Yi et al., 2000; Liu et al., 1996; Hara et al., 1997). Among the several hydrophobizing candidates investigated was DOTAP (1,2-dioleoyl-sn-glycero-3-trimethyl-ammonium-propane), an ester-linked biodegradable lipid. A DOTAP/plasmid DNA complex (1.5:1−/+verify) with plasmid DNA at a final concentration of 40 µg/mL was added to the following 1 mL total volume formulation: emulsifying wax (2 mg), Brij 78 (10 mM), and 50 µL of Tween 20 (1:3 w/w diluted with water). The formulation was briefly heated to 52° C. to form an O/W microemulsion and then cooled to 25° C. to form nanoparticles containing plasmid DNA. The nanoparticle size was measured as 58.5±26.8 nm. To verify that plasmid DNA was entrapped in the nanoparticles, an identical formulation was made using fluorescein labeled plasmid DNA (final 20 µg/mL). Formed nanoparticles were purified via Sephadex-G75 gel permeation chromatography and the fractions were detected using photon correlation spectroscopy (to obtained light scattering result, cps) or fluorescence spectroscopy (to obtained plasmid DNA concentration). The results as shown in FIG. 22 show that fluorescein labeled plasmid DNA did elute in the same fractions as those of solid nanoparticles. To further confirm that the plasmid DNA is entrapped in the solid nanoparticles and not adsorbed onto the nanoparticles, the preparation was treated with DNase I, a nuclease that rapidly degrades plasmid DNA. The results as shown in FIG. 23 demonstrate that nuclease treatment for 15 minutes at 37° C. failed to degrade plasmid DNA and suggest that plasmid DNA was entrapped in the cured 58 nm nanoparticles.

EXAMPLE 19

Preparation of liquid hydrocarbon-in-fluorocarbon microemulsion precursors: To demonstrate that liquid matrix in perflubron microemulsions can be formed, the following experiment was completed. PDFOA (94.7 mg) was added to 500 µL perflubron in a scintillation vial under gentle magnetic stirring. PDFOA did not dissolve in perflubron at 25° C. White beeswax, USP (33.4 mg) was added as a solid to the PDFOA suspended in the stirring perflubron. The vial was heated to 60° C. and the mixture became a clear homogenous solution. The mixture was removed from heat and within 1 minute the mixture slowly turned opaque. After 5 minutes, the precipitated wax agglomerated into a clump. As a control, the experiment was completed without the PDFOA. Melted wax and perflubron were not miscible at 60° C. indicating that the fluorosurfactant was needed. The results demonstrated that liquid matrix O/F microemulsion was possible, but that a more suitable nanoparticle matrix material (that did not agglomerate) was needed.

UTILITY

The application relates to new and improved methods to engineer useful nanoparticulate systems that may solve many of the hurdles associated with conventional technologies and provide unique research opportunities across many different fields. The invention involves the use of microemulsion precursors (ethanol-in-fluorocarbon, liquid hydrocarbon-in-fluorocarbon, or liquid hydrocarbon-in-water) to engineer useful nanoparticles. The engineered nanoparticulate systems may contain many different materials for various medical and engineering applications such as plasmid DNA for gene therapy and genetic vaccines, magnetic substances for use as nanomagnets, or chemical, thermal, or biological sensors for use as nanosensors. An additional advantage of this invention over prior art is that the described nanoparticle systems can be engineered rapidly, reproducibly, and cost-effectively from the microemulsion precursors in a one-step process and contained in one manufacturing vessel, vial, or container.

All of the references cited in the application are incorporated herein by reference in their entirety.

Those skilled in the art will recognize, or be able to ascertain using no more than routine experimentation, many equivalents to the specific embodiments of the invention specifically described herein. Such equivalents are intended to be encompassed in the scope of the following claims.

REFERENCES

Agostiano, A., Catalano, M., Curri, M. L., Della Monica, M., Manna, L., Vasanelli, L. Synthesis and structural characterisation of CdS nanoparticles prepared in a four-components "water-in-oil" microemulsion, *Micron*, 31:253–258, 2000.

Ando, S., Putnam, D, Pack, D. W., Langer, R. PLGA microspheres containing plasmid DNA: preservation of supercoiled DNA via cryopreparation and carbohydrate stabilization. *J. Pharm. Sci.* 88:126–30, 1999.

Bhargava, H. N., Narurkar, A., Lieb, L. M. Using microemulsions for drug delivery. *Pharm. Tech.* March 1987, pp. 46–53.

Bocca, C., Caputo, O., Cavalli, R., Gabriel, L., Miglietta, A., Gasco, M. R. Phagocytic uptake of fluorescent stealth and non-stealth solid lipid nanoparticles, *International Journal of Pharmaceutics*, 175: 185–193, 1998.

Braun, R. Babiuk, L. A., and van Brunen Little-Van den hurk, S. Enhanced immune response to an intradermally delivered DNA vaccine expressing a secreted form of BHV-1 gD. *Vaccine Res.* 6 (1998) 151–164.

Capek, I. Microemulsion polymerization of styrene in the presence of anionic emulsifier, *Advances in Colloid and Interface Science*, 82: 253–273, 1999.

Cavalli, R., Peira, E., Caputo, O., Gasco, M. R. Solid lipid nanoparticles as carriers of hydrocortisone and progesterone complexes with cyclodextrins, *International Journal of Pharmaceutics*, 182:59–69, 1999.

Constantinides, P. P. Lipid microemulsions for improving drug dissolution and oral absorption: physical and biopharmaceutical aspects. *Pharm. Res.* 12:1561–1572, 1995.

Cornelus, C., Krafft, M. P., Riess, J. G. Improved control over particle sizes and stability of concentrated fluorocarbon emulsions by using mixed fluorocarbon/hydrocarbon molecular dowels. *Artif. Cells Blood Sub. Immobil. Biotech.* 22:1183–1191, 1994.

Corr, M., Lee, D. J., Carson, D. A., and Tighe, H. Gene vaccination with naked plasmid DNA: mechanism of CTL priming. *J. Exp. Med.* 184 (1996) 1555–1560.

Corr, M., von Damm, A., Lee, D. J., Tighe, H. In vivo priming by DNA injection occurs predominantly by antigen transfer. *J. Immunol.* 163 (1999) 4721–4727.

Degano, P., Sarphie, D. F., Bangham, C. R., Intradermal DNA immunization of mice against influenza A virus using the novel Powderject system. *Vaccine* 16 (1998) 394–398.

Doe, B., Selby, M., Barnett, S., Baenziger, J., and Walker, C. M. Induction of cytotoxic T lymphocytes by intramuscular immunization with plasmid DNA is facilitated by bone marrow-derived cells. *Proc. Natl. Acad. Sci. USA* 93 (1996) 8578–8583.

Douglas, S. J., Davis, S. S., Illum, L. Nanoparticles in drug delivery. *Crit. Rev. Ther. Drug Carrier. Syst.* 3:233–261, 1987.

Fan, H., Lin, Q., Morrissey, G. R., Khavari, P. A. Immunization via hair follicles by topical application of naked DNA to normal skin. Nat Biotechnol. 17 (9) (1999) 870–872.

Fang, J., Stokes, K. L., Wiemann, J., Zhou, W. Nanocrystalline bismuth synthesized via an in situ polymerization microemulsion process, *Materials Letters*, 42:113–120, 2000.

Fynan, E. F., Webster, R. G., Fuller, D. H., Haynes, J. R., Santoro, J. C., Robinson, H. L. DNA vaccines: protective immunizations by parental, mucosal and gene-gun inoculations. *Proc. Natl, Acad. Sci. USA* 90 (1993) 11478–11482.

Gauger, P. G., Pranikoff, T., Schreiner, R. J., Moler, F. W., Hirschl, R. B. Initial experience with partial liquid ventilation in pediatric patients with the acute respiratory distress syndrome. *Crit. Care Med.* 24:16–22, 1996.

Gerdts, V., Jons, A., Makoschey, B., Visser, N., Mettenleiter, T. C., Protection of pigs against Aujeszky's disease by DNA vaccination *J Gen Virol.* 78 (Pt 9) (1997) 2139–46.

Hara, T., Tan, Y., Huang, L. In vivo gene delivery to the liver using reconstituted chylomicron remnants as a novel nonviral vector. *Proc. Natl. Acad. Sci.* 94:14547–14552, 1997.

Ho H. O., Hsiao, C. C., Sheu, M. T. Preparation of microemulsions using polyglycerol fatty acid esters as surfactant for the delivery of protein drugs. *J. Pharm. Sci.* 85:138–143, 1996.

Huang, A. Y. C., Golumbek, P., Ahmadzadeh, M., Jaffee, E., Pardoll, D., and Levitsky, H. Role of bone marrow derived cells in presenting MHC class I-restricted tumor antigens. *Science* 264 (1994)961–965.

Jono, K., Ichikawa, H., Fujioka, K., Fukumori, Y., Akine, Y., Tokuuye, K. Preparation of lecithin microcapsules by a dilution method using the Wurster process for intraarterial administration in gadolinium neutron capture therapy. *Chem. Pharm. Bull.* 47(1):54–63, 1999.

Kreuter, J. Nanoparticles as adjuvants for vaccines. *Pharm. Biotechnol.* 6:463–472, 1995.

Kwoh, D. Y., Coffin, C. C., Lollo, C. P., Jovenal, J., Banaszczyk, M. G., Mullen, P., Phillips, A., Amini, A., Fabrycki, J., Bartholomew, R. M., Brostoff, S. W., Carlo, D. J. Stabilization of poly-L-lysine/DNA polyplexes for in vivo gene delivery to the liver. *Biochim. Biophys. Acta.* 1444:171–190, 1999.

Lade, M., Mays, H., Schmidt, J., Willumeit, R., Schomäcker, R. On the nanoparticle synthesis in microemulsions: detailed characterization of an applied reaction mixture, Colloids and Surfaces A: Physicochemical and Engineering Aspects, 163:3–15, 2000.

Lattes, A., Rico-Lattes, I. Microemulsions of perfluorinated and semi-fluorinated compounds. Art. Cells. Blood Subs. Immob. Biotech. 22:1007–1018, 1994.

Levine, M. M., Woodrow, G. C., Kaper, J. B., and Cobon, G. S. New Generation Vaccines, Marcel Dekker, Inc. New York, N.Y., 1997.

Li, Y., Park, C. W. Particle size distribution in the synthesis of nanoparticles using microemulsions, Langmuir, 15: 952–956, 1999.

Liu, M. A., Hilleman, M. R., and Kurth, R. DNA Vaccines: A New Era in Vaccinology, Ann. N.Y. Acad. Sci. New York, N.Y., Vol. 772, 1995.

Liu, M. A. The immunologist's grail: Vaccines that generate cellular immunity. Proc. Natl. Acad. Sci. USA. 94:10496–10498, 1997.

MacLaughlin, F. C., Mumper, R. J., et al. Chitosan and depolymerized chitosan oligomers as condensing carriers for in-vivo plasmid delivery. J. Controlled Rel. 56:259–272, 1998.

Mandeville, J. B., Moore, J., Chesler, D. A., Garrido, L., Weissleder, R., Weisskoff, R. M. Dynamic liver imaging with iron oxide agents: effects of size and biodistribution on contrast. Magn. Reson. Med. 37:885–890, 1997.

Meier, W. Nanostructure synthesis using surfactants and copolymers, Current Opinion in Colloid & Interface Science, 4:6–14, 1999.

Meijer, D. K. F., Molema, G. Targeting of drugs to the liver. Sem. Liv. Dis. 15:202–256, 1995

Miyamoto, M., Hirano, K., Ichikawa, H., Fukumori, Y., Akine, Y., Tokuuye, K. Biodistribution of gadolinium incorporated in lipid emulsions intraperitoneally administered for neutron-capture therapy with tumor-bearing hamsters. Biol. Pharm. Bull. 22(12): 1331–1340, 1999.

Mumper, R. J., Ledebur, H. C., Rolland, A. P., Tomlinson, E. Controlled Plasmid Delivery and Gene Expression: Applications for Nucleic Acid-Based Vaccines. In: DNA Vaccines: Methods and Protocols. D B Lowrie and R Whalen (Eds.). Humana Press, Inc., Totowa, N.J., 1999. Chapter 24, pp. 267–286.

Mumper, R. J., Ledebur, H. C. Dendritic cell delivery of plasmid DNA: Application for controlled nucleic acid-based vaccines, in: J. M. Walker (Ed.), Molecular Biology and Biotechnology, 2001, in press.

Mumper, R. J., Klakamp, S. L. Polymeric Gene Delivery Systems for In-Vivo Gene Therapy. In: Advanced Gene Delivery: From Concepts to Pharmaceutical Products. AP Rolland (Ed.). Harwood Academic Publishers, Amsterdam, The Netherlands. (1999). pp. 143–173.

Munshi, N., De, T. K., Maitra, A. Preparation and size modulation of drug loaded nanoencapsulated particles using microemulsion mediated method, Journal of Controlled Release, 41:S7, 1997.

Pertmer, T. M., Eisenbraun, M. D., McCabe, D., Prayaga, S. K., Fuller, D. H., Haynes, J. R. Gene gun-based nucleic acid immunization: elicitation of humoral and cytotoxic T lymphocytes responses following epidermal delivery of nanogram quantities of DNA. Vaccine 13 (1995) 1427–1430.

Plank, C., Zatloukal, K., Cotton, M., Mechtler, K., Wagner, E. Gene transfer into hepatocytes using asialoglycoprotein receptor mediated endocytosis of DNA complexed with an artificial tetra-antennary galactose ligand. Bioconj. Chem. 3:533–539, 1992.

Porta, F., Bifulco, C., Fermo, P., Bianchi, C. L., Fadoni, M., Prati, L. Synthesis of spherical nanoparticles of $Cu_2L_2O_5$ (L=Ho, Er) from W/O microemulsions, Colloids and Surfaces A: Physicochemical and Engineering Aspects, 160:281–290, 1999.

Riess, J. G., Krafft, M. P. Advanced fluorocarbon-based systems for oxygen and drug delivery, and diagnosis. Art. Cells. Blood Subs. Immob. Biotech. 25:43–52, 1997.

Robinson, H. L., and Torres, C. A. T. DNA vaccines. Sem. Immunology. 9:271–283, 1997.

Ruys, A. J., Mai, Y. W. The nanoparticle-coating process: a potential sol-gel route to homogeneous nanocomposites, Materials Science and Engineering 265:202–207, 1999.

Schlepper-Schafer, J., Hulsmann, D., Djovkar, A., Meyer, H. E., Herbertz, L., Kolb, H., Kolb-Bachofen, V. Endocytosis via galactose receptors in vivo. Ligand size directs uptake by hepatocytes and/or liver macrophages. Exp. Cell Res. 165:494–506, 1986.

Shi, Z., Curiel, D. T., Tang, D. C. DNA-based non-invasive vaccination onto the skin. Vaccine 17 (17) (1999) 2136–41.

Singh, M., Briones, M., Ott, G., O'Hagan, D. Cationic microparticles: A potent delivery system for DNA vaccines. Proc. Natl. Acad. Sci. USA 97 (2) (2000) 811–6.

Sliedregt, L. A., Rensen, P. C., Rump, E. T., van Santbrink, P. J., Bijsterbosch, M. K., Valentijn, A. R., van der Marel, G. A., van Boom, J. H., van Berkel, T. J., Biessen, E. A. Design and synthesis of novel amphiphilic dendritic galactosides for selective targeting of liposomes to the hepatic asialoglycoprotein receptor. J. Med. Chem. 25:609–618, 1999.

Song, K. C., Kang, Y. Preparation of high surface area tin oxide powders by a homogeneous precipitation method, Materials Letters, 42:283–289, 2000.

Tang, Z., Liu, S., Wang, Z., Dong, S., Wang, E. Electrochemical synthesis of polyaniline nanoparticles, Electrochemistry Communications, 2:32–35, 2000.

Tang, D. C., Shi, Z., Curiel, D. T. Vaccination onto bare skin. Nature 388 (1997) 729–30.

Tang, D. C., DeVit, M., Johnston, S. A. Genetic immunization is a simple method for eliciting an immune response. Nature 356 (1992) 152–154.

Tojo, C., Blanco, M. C., Lopez-Quintela, M. A. Influence of reactant excess and film flexibility on the mechanism of nanoparticle formation in microemulsions: A Monte Carlo simulation, Langmuir, 14:6835–6839, 1998.

Tokumitsu, H., Hiratsuka, J., Sakurai, Y., Kobayashi, T., Ichikawa, H., Fukumori, Y. Gadolinium neutron-capture therapy using novel gadopentetic acid-chitosan complex nanoparticles: in vivo growth suppression of experimental melanoma solid tumor. Cancer Lett. 2000 150(2):177–182, 2000.

Tokumitsu, H., Ichikawa, H., Fukumori, Y. Chitosan-gadopentetic acid complex nanoparticles for gadolinium neutron-capture therapy of cancer: preparation by novel emulsion-droplet coalescence technique and characterization. Pharm Res. 16(12): 1830–1835, 1999.

Torres, C. A. T., Iwasaki, A. Barber, B. H., and Robinson, H. L. Differential dependence on target site tissue for gene gun and intramuscular DNA immunizations. J. Immunol. 158 (1997) 4529–4532.

Truong-Le, V. L., August, J. T., Leong, K. W. Controlled gene delivery by DNA-gelatin nanospheres. Hum. Gene Ther. 10:1709–1717, 1998.

Ulmer, J. B., Sadoff, J. C., and Liu, M. A. DNA vaccines, Cur. Opin. Immunol. 8 (1996) 531–536.

Ulmer, J. B., Deck, R. R., Dewitt, C. M., Donnelly, J. I., and Liu, M. A. Generation of MHC class I-restricted cytotoxic T lymphocytes by expression of a viral protein in muscle cells: antigen presentation by non-muscle cells. Immunology 89 (1996) 59–67.

Van Drunen Little-van den hurk, S., Braun, R. P., Lewis, P. J., Harvonen, B. C., Baca-Estrada, M. E., Snider, M., McMartney, D., Watts, T., and Babiuk, L. A. Intradermal immunization with a bovine herpesvius-1 DNA vaccine induces protective immunity in cattle. *J. Gen. Viol.* 79 (1998) 831–839.

Van Rooij, E. M., Haagmans, B. L., de Visser, Y. E., de Bruin, M. G., Boersma, W., Bianchi, A. T. Effect of vaccination route and composition of DNA vaccine on the induction of protective immunity against pseudorabies infection in pigs. *Vet Immunol Immunopathol*, 66 (2) (1998) 113–26.

Wadhwa, M. S., Rice, K. G. Receptor mediated glycotargeting. *J. Drug Target.* 3:111–127, 1995.

Wang, D., Robinson, D. R., Kwon, G. S., Samuel, J. Encapsulation of plasmid DNA in biodegradable poly(D, L-lactic-co-glycolic acid) microspheres as a novel approach for immunogene delivery. *J Cont. Rel.* 57:9–18, 1999.

Wu, G. Y., Wu, C. H. Receptor-mediated gene delivery and expression in vivo. *J. Biol. Chem.* 263:14621–14624, 1988.

Xiangling, X., Xuewu, G., Qiang, Y., Zhicheng, Z., Ju, Z., Aizhen, N., Manwei, Z. Growth of polymer nanoparticles in microemulsion polymerization initiated with ray, *Radiation Physics and Chemistry*, 54: 279–283, 1999.

Yoshida, A., Nagata, T., Uchijima, M., Higashi, T., Koide, Y. Advantage of gene gun-mediated over intramuscular inoculation of plasmid DNA vaccine in reproducible induction of specific immune responses. *Vaccine* 18 (17) (2000) 1725–9.

What is claimed is:

1. A method of making solid nanoparticles, comprising:
    making an oil-in-water microemulsion by heating, the microemulsion comprising:
        a liquid nanoparticle matrix material formed by heating a solid matrix material until melted;
        a surfactant or a co-surfactant or a mixture thereof, and
        a molecule of interest, wherein the molecule is a drug molecule;
    wherein the microemulsion is formed essentially spontaneously by heating at a temperature of between about 35° C. and about 100° C.; and
    cooling the microemulsion while stirring to form solid nanoparticles having a diameter of less than about 300 nanometers, wherein said solid nanoparticles are formed by cooling the microemulsion without aqueous dilution, and where the molecule of interest is either entrapped in or adsorbed to the solid nanoparticles.

2. The method according to claim 1, wherein the nanoparticle matrix material comprises one or more of the following materials: emulsifying wax, polyoxyethylene sorbitan fatty acid esters, polyoxyethylene alkyl ethers, polyoxyethylene stearates, phospholipids, fatty acids or fatty alcohols or their derivatives, or combinations thereof.

3. The method according to claim 1, wherein the liquid nanoparticle matrix material is present in the microemulsion at a concentration from about 0.1 to about 30 mg/mL.

4. The method according to claim 1, wherein the microemulsion comprises an oil phase that is present as liquid droplets having a diameter of less than about 100 nanometers.

5. The method according to claim 1, wherein the microemulsion comprises a continuous phase comprising water or an aqueous buffer at a concentration of greater than about 95% w/w.

6. The method according to claim 1, wherein the surfactant or co-surfactant comprises polyoxyethylene alkyl ethers, polyoxyethylene sorbitan fatty acid esters, polyoxyethylene stearates, hexadecyltrimethylammonium bromide, fatty alcohol and their derivatives, or combinations, thereof.

7. The method according to claim 1, wherein the surfactant is present at a total concentration of about 1–5000 mM.

8. The method according to claim 1, wherein the molecule of interest is present at a total concentration in the range of about 20 μg/mL to about 5 mg/mL.

9. The method according to claim 1, wherein the nanoparticle is coated with a cell-specific ligand such as an antibody, carbohydrate, peptide, protein, or derivatives or combinations thereof.

10. The method of claim 1, wherein the nanoparticles and molecule of interest are formulated into a pharmaceutical composition suitable for intravenous, intramuscular or subcutaneous administration.

* * * * *